(12) United States Patent
Yamamoto et al.

(10) Patent No.: US 8,297,975 B2
(45) Date of Patent: Oct. 30, 2012

(54) REACTION-CURABLE ADHESIVE COMPOSITION AND DENTAL ADHESIVE KIT

(75) Inventors: Takashi Yamamoto, Moriyama (JP); Toshiki Ono, Moriyama (JP); Masami Arata, Moriyama (JP); Tatsuya Ori, Moriyama (JP)

(73) Assignee: Sun Medical Co., Ltd., Moriyama-shi (JP)

( * ) Notice: Subject to any disclaimer, the term of this patent is extended or adjusted under 35 U.S.C. 154(b) by 251 days.

(21) Appl. No.: 12/599,821

(22) PCT Filed: May 14, 2008

(86) PCT No.: PCT/JP2008/058868
§ 371 (c)(1),
(2), (4) Date: Nov. 12, 2009

(87) PCT Pub. No.: WO2008/140103
PCT Pub. Date: Nov. 20, 2008

(65) Prior Publication Data
US 2010/0292359 A1 Nov. 18, 2010

(30) Foreign Application Priority Data
May 15, 2007 (JP) ................................ 2007-129346

(51) Int. Cl.
*A61K 6/00* (2006.01)
*A61K 6/083* (2006.01)

(52) U.S. Cl. ......... 433/226; 433/228.1; 522/24; 522/28; 522/48; 522/60; 522/182; 523/115; 523/116; 523/118

(58) Field of Classification Search ................ 522/14, 522/24, 28, 29, 78, 84, 171, 48, 60, 64, 180, 522/182; 523/115–118; 433/226, 228.1
See application file for complete search history.

(56) References Cited

U.S. PATENT DOCUMENTS

| | | | |
|---|---|---|---|
| 4,182,035 A * | 1/1980 | Yamauchi et al. ......... 433/228.1 |
| 4,243,763 A * | 1/1981 | Argentar ........................ 525/27 |
| 4,778,834 A * | 10/1988 | Murray ........................ 523/212 |
| 5,530,038 A | 6/1996 | Yamamoto et al. |
| 5,587,406 A | 12/1996 | Yamamoto et al. |
| 5,707,611 A * | 1/1998 | Ikemura et al. ................. 424/53 |
| 5,834,532 A | 11/1998 | Yamamoto et al. |
| 6,071,983 A | 6/2000 | Yamamoto et al. |
| 6,191,191 B1 * | 2/2001 | Harada et al. ................. 523/115 |
| 6,288,138 B1 * | 9/2001 | Yamamoto et al. ........... 523/118 |
| 6,583,197 B1 * | 6/2003 | Wada et al. .................... 522/84 |
| 6,869,984 B2 | 3/2005 | Kawashima et al. |
| 7,879,924 B2 * | 2/2011 | Torii et al. .................... 523/116 |
| 7,963,769 B2 * | 6/2011 | Qian ........................ 433/228.1 |
| 2003/0083398 A1 | 5/2003 | Kawashima et al. |
| 2007/0259988 A1 * | 11/2007 | Dorsman et al. ............. 523/118 |
| 2009/0137697 A1 | 5/2009 | Ori et al. |

FOREIGN PATENT DOCUMENTS

| | | |
|---|---|---|
| JP | 6040838 A | 2/1994 |
| JP | 7082115 A | 3/1995 |
| JP | 7097306 A | 4/1995 |
| JP | 7291819 A | 11/1995 |
| JP | 2003012430 A | 1/2003 |
| JP | 2003238325 A | 8/2003 |
| WO | 2007018220 A1 | 2/2007 |

* cited by examiner

*Primary Examiner* — Susan W Berman
(74) *Attorney, Agent, or Firm* — The Webb Law Firm

(57) ABSTRACT

A reaction-curable adhesive composition exhibiting acidity is formed form a weakly acidic to alkaline composition (I) comprising (a) a polymerizable monomer and (b) a compound represented by the following formula (I) and a strongly acidic composition (II) comprising (a) a polymerizable monomer.

$$R^1\text{—}C_6H_4\text{—}NR^2CH_2COOR^3 \qquad (1)$$

wherein $R^1$ and $R^2$ are each independently a hydrogen atom or an alkyl group which may have a functional group, and $R^3$ is a hydrogen atom or a metal atom. The composition containing the polymerizable monomer can be stably stored for a long period of time.

21 Claims, No Drawings

REACTION-CURABLE ADHESIVE COMPOSITION AND DENTAL ADHESIVE KIT

TECHNICAL FIELD

The present invention relates to a reaction-curable adhesive composition preferable as a dental adhesive, a coating material or a sealant, and a dental adhesive kit using the composition. More particularly, the invention relates to a curable adhesive composition of a dental adhesive employable for teeth, metals, ceramics, cements, resins and composite resin materials, a primer composition suitable for the composition, and a product kit.

BACKGROUND ART

Dental adhesives such as bonding materials and cements are divided, based on the curing mechanism, into dental adhesives of photopolymerization type which are polymerized and cured by irradiating them with visible rays and dental adhesives of chemical polymerization type which are polymerized and cured by mixing two or more compositions separately stored, immediately before using.

The performance of the dental adhesives of photopolymerization type bonded to tooth substances has been rapidly improved in recent years. The reason is considered to be that polymerization inhibition by oxygen in air in the polymerization process is relatively small by virtue of this curing mechanism and even under the acidic conditions the rate of polymerization is enhanced. On the other hand, in order to cure the dental adhesives of photopolymerization type, presence of light is an essential requisite, so that in the case where an adhesive is applied to the place which light hardly reaches, it is necessary to use a dental adhesive of chemical polymerization type.

A large number of proposals relating to the dental adhesives of chemical polymerization type have been made so far, but as compared with the performance of the dental adhesives of photopolymerization type, performance of the dental adhesives of chemical polymerization type cannot be said to be satisfactory. The reason is considered to be that the polymerization initiation efficiency of a polymerization initiator used is low under the acidic conditions, and in the polymerization process, the dental adhesives of chemical polymerization type are subject to polymerization inhibition by oxygen, so that the rate of polymerization is not sufficiently enhanced.

For such dental adhesives of chemical polymerization type, there has been made a proposal of using a polymerization initiator which is easily polymerized and cured even under the acidic conditions (patent document 1 (Japanese Patent Laid-Open Publication No. 97306/1995)). Further, in order that a dental adhesive may hardly suffer polymerization inhibition by oxygen in the polymerization process, there has been made a proposal of increasing viscosity of a dental adhesive or using a paste of high viscosity by mixing a dental adhesive with a filler or the like (patent document 2 (Japanese Patent Laid-Open Publication No. 291819/1995)).

In the patent document 1, an adhesive curable composition which is cured through chemical polymerization by mixing a liquid composition with a powder composition immediately before using has been proposed, but it has been indicated that when N-phenylglycine (NPG) used as one component of a polymerization initiator is mixed with a polymerizable monomer, gelation takes place in a short period of time.

In the patent document 2, there has been proposed an adhesive curable composition which is used in the following manner. That is to say, N-phenylglycine (NPG) or sodium p-toluenesulfinate (p-TSNa) used as one component of a polymerization initiator is adsorbed on a jig or the like and stored, while the composition containing a polymerizable monomer and a filler is stored in the form of a paste, and the paste in a given amount and the jig having adsorbed the polymerization monomer, etc. are brought into contact with each other immediately before using. In this proposal, it is necessary to prepare jigs with different adsorbed amounts according to the amounts of the adhesive curable composition used, and in the case of a jig with a fixed adsorbed amount, there is a problem that the amount of the adhesive curable composition used is markedly restricted. Together with this proposal, a method of storing a mixture of NPG and a polymerizable monomer having an oxyethylene chain in a molecule has been proposed.

However, if such a composition is stored for a long period of time, the composition is discolored, and a color tone of a cured product is sometimes impaired.

It is an object of the present invention to provide a reaction-curable adhesive composition containing a composition capable of stably storing a polymerizable monomer over a long period of time, said polymerizable monomer generally undergoing gelation reaction in a short period of time, suffering occurrence of extreme discoloration and being considered to have bad storage stability.

It is another object of the present invention to provide a dental adhesive kit using such a stabilized reaction-curable adhesive composition as above and having excellent long-term storage stability.

SUMMARY OF THE INVENTION

The reaction-curable adhesive composition of the present invention is a reaction-curable adhesive composition exhibiting acidity, which comprises:

a weakly acidic to alkaline composition (I) comprising (a) a polymerizable monomer and (b) a compound represented by the following formula (1):

$$R^1\text{—}C_6H_4\text{—}NR^2CH_2COOR^3 \qquad (1)$$

wherein $R^1$ and $R^2$ are each independently a hydrogen atom or an alkyl group which may have a functional group, and $R^3$ is a hydrogen atom or a metal atom, and a strongly acidic composition (II) comprising (a) a polymerizable monomer.

The reason why the composition of the invention containing a component having reactivity can be stored for a long period of time is that the weakly acidic to alkaline composition (I) can be kept in a more stable state by allowing an alkali metal or an alkaline earth metal to coexist in the component contained in the weakly acidic to alkaline composition (I).

The dental adhesive kit of the present invention comprises:

a weakly acidic to alkaline composition (I) comprising (a) a polymerizable monomer and (b) a compound represented by the following formula (1):

$$R^1\text{—}C_6H_4\text{—}NR^2CH_2COOR^3 \qquad (1)$$

wherein $R^1$ and $R^2$ are each independently a hydrogen atom or an alkyl group which may have a functional group, and $R^3$ is a hydrogen atom or a metal atom, a strongly acidic composition (II) comprising (a) a polymerizable monomer, and a primer composition (III), wherein the primer composition (III) comprises (a) a polymerizable monomer, (e) an aromatic tertiary amine and (f) a water-soluble solvent, and the weakly acidic to alkaline composition (I), the strongly acidic composition (II) and the primer composition (III) are separately packaged.

In the use of such a dental adhesive kit, the composition (I) and the composition (II) are usually kneaded to make them curable immediately before using. The composition (I) and the composition (II) are usually packaged separately from each other, and before using, they are taken out in given amounts and kneaded with each other, whereby they become usable.

For various purposes, dental materials are sometimes obliged to be stored in such a state that a polymerizable monomer has been mixed with other substances such as organic acid or its salt. However, when the polymerizable monomer and other components such as organic acid are allowed to coexist for a long period of time as above, it becomes difficult to stably keep the polymerizable monomer, and at least a part of the polymerizable monomer undergoes reaction during the storage, so that it becomes difficult to form a homogenous polymer after long-term storage.

Paying attention to the long-term stability of the polymerizable monomer, it has been studied to allow the polymerizable monomer and other components such as organic acid or its salt to coexist. As a result, it has been found that the polymerizable monomer can be stably kept for a long period of time by allowing the polymerizable monomer and an alkali component such as an alkali metal or an alkaline earth metal to coexist or by maintaining the pH value of the composition on the weakly acidic to alkaline side. That is to say, by using an alkali metal or an alkaline earth metal to allow it to exist so as to preferably neutralize an acidic group of the monomer having an acidic group, the pH value of the composition (I) can be maintained in the weakly acidic to alkaline range as above, whereby the composition (I) can be stably kept for a long period of time.

According to the reaction-curable adhesive composition of the present invention, gelation or marked coloring caused by reaction of a polymerizable monomer can be prevented in the case where the polymerizable monomer and other components such as a metal or a metal salt are contained.

That is to say, in the reaction-curable adhesive composition exhibiting acidity of the present invention, the pH value of the composition (I) has been adjusted to weakly acidic to alkaline, so that even if the reaction-curable adhesive composition is stored for a long period of time, partial polymerization reaction of the polymerizable monomer contained in the composition (I) does not proceed, and the reaction-curable adhesive composition exhibiting acidity which is obtained by kneading the composition (I) with the strongly acidic composition (II) shows extremely high bond property to teeth. Moreover, by packaging them separately, control of the amounts used or change of the curing time becomes easy, and dental restoration can be efficiently and rapidly promoted, so that the burden on the patient is reduced.

BEST MODE FOR CARRYING OUT THE INVENTION

Next, the reaction-curable adhesive composition exhibiting acidity and the dental adhesive composition of the invention are described in detail.

The reaction-curable adhesive composition exhibiting acidity of the invention is formed from a weakly acidic to alkaline composition (I) and a strongly acidic composition (II).

The weakly acidic to alkaline composition (I) contains (a) a polymerizable monomer and (b) a compound represented by the following formula (1).

$$R^1-C_6H_4-NR^2CH_2COOR^3 \qquad (1)$$

In the formula (1), $R^1$ and $R^2$ are each independently a hydrogen atom or an alkyl group which may have a functional group. $R^3$ is a hydrogen atom or a metal atom. A compound of the formula (1) wherein $R^1$ is a hydrogen atom, $R^2$ is also a hydrogen atom, and $R^3$ is a hydrogen atom is N-phenylglycine (NPG). Examples of the compounds represented by the formula (1) include the above-mentioned N-phenylglycine, its salts, N-triglycine and its salts. These compounds can be used singly or in combination. As the compound (b) represented by the formula (1), N-phenylglycine (NPG) or an alkali metal salt thereof, particularly a sodium salt (NPG-Na) of N-phenylglycine (NPG), is preferable in the invention.

Examples of the polymerizable monomers (a) contained in the weakly acidic to alkaline composition (I) for use in the invention include aliphatic esters of (meth)acrylic acid, polyethylene glycol di(meth)acrylates, polypropylene glycol di(meth)acrylates, mono(meth)acrylates wherein any one of acryloyl groups in polyalkylene glycol is substituted by an alkyl group, (meth)acrylates having a urethane bond, a (meth)acrylic acid condensate of bisphenol A condensed with oxyalkylene, styrene derivatives, vinyl acetate derivatives, a monomer having a hydroxyl group-containing (meth)acryloyl group, a polymerizable monomer having an acidic group in a molecule, and a monomer wherein an acidic group in a molecule is neutralized. In the present invention, the term "(meth)acrylic" is a broader term including "acrylic" and "methacrylic".

Specific examples of the polymerizable monomers (a) in the invention include the compounds described below.

Examples of the polymerizable monomers (a) for use in the invention include:

aliphatic esters of (meth)acrylic acid, such as methyl (meth)acrylate, ethyl(meth)acrylate, propyl(meth)acrylate, butyl (meth)acrylate, neopentyl glycol di(meth)acrylate and trimethylolpropane tri(meth)acrylate;

polyethylene glycol di(meth)acrylates, such as ethylene glycol di(meth)acrylate, diethylene glycol di(meth)acrylate, triethylene glycol di(meth)acrylate, pentaethylene glycol di(meth)acrylate, nonaethylene glycol di(meth)acrylate and tetradecaethylene glycol di(meth)acrylate;

polypropylene glycol di(meth)acrylates, such as propylene glycol di(meth)acrylate, dipropylene glycol di(meth)acrylate, tripropylene glycol di(meth)acrylate and nonapropylene glycol di(meth)acrylate;

mono(meth)acrylates wherein any one of the (meth)acryloyl groups in the above-mentioned polyethylene glycol di(meth)acrylates and polypropylene glycol di(meth)acrylates is substituted by a methyl group, an ethyl group or the like;

(meth)acrylates having a urethane bond, such as an addition product of any one of 2-(meth)acryloyloxyethyl isocyanate, 2,2,4-trimethylhexamethylene diisocyanate and 1,3,5-trimethylhexamethylene diisocyanate with 2-hydroxyethyl (meth)acrylate;

2,2-bis(4-(meth)acryloyloxypolyethoxyphenyl)propanes obtained by further condensing an addition product of bisphenol A with oxyethylene, with (meth)acrylic acid;

styrene derivatives, such as styrene, 4-methylstyrene, 4-chloromethylstyrene and divinylbenzene; and vinyl acetate.

These polymerizable monomers can be used singly or in combination.

As the polymerizable monomer (a) for use in the invention, further, a monomer having, in a molecule, a (meth)acryloyl group having a hydroxyl group is also employable. Examples of such polymerizable monomers having a hydroxyl group include:

hydroxyl group-containing (meth)acrylates, such as 2-hydroxyethyl(meth)acrylate (in the case of methacrylate: HEMA), 2-hydroxypropyl(meth)acrylate, 3-hydroxypropyl (meth)acrylate, 4-hydroxybutyl(meth)acrylate, 5-hydroxypentyl(meth)acrylate, 6-hydroxyhexyl(meth)acrylate, 10-hydroxydecyl(meth)acrylate, 1,2- or 1,3- or 2,3-dihydroxypropane (meth)acrylate, diethylene glycol mono (meth)acrylate, triethylene glycol mono(meth)acrylate, pentaethylene glycol mono(meth)acrylate, polyethylene glycol mono(meth)acrylate and dipropylene glycol mono(meth) acrylate;

hydroxyl group-containing (meth)acrylamides, such as methylol (meth)acrylamide, N-(meth)acryloyl-2,3-dihydroxypropylamine and N-(meth)acryloyl-1,3-dihydroxypropylamine;

2-hydroxy-3-phenoxypropyl(meth)acrylate (in the case of methacrylate: HPPM) and 2-hydroxy-3-naphthoxypropyl (meth)acrylate (in the case of methacrylate: HNPM); and addition products of GMA with aliphatic or aromatic polyols (including phenol), such as an addition reaction product (in the case of methacrylate: Bis-GMA) of 1 mol of bisphenol A with 2 mol of glycidyl (meth)acrylate (in the case of methacrylate: GMA).

These polymerizable monomers can be used singly or in combination.

As the polymerizable monomer (a) for use in the invention, furthermore, a polymerizable monomer (a1) containing an acidic group in a molecule is also employable. This polymerizable monomer (a1) containing an acidic group in a molecule has, as a polymerizable group, a radical-polymerizable unsaturated group having a (meth)acryloyl group, a styryl group, a vinyl group, an allyl group or the like. The polymerizable monomer (a1) containing a carboxyl group in a molecule has only to have at least one of, for example, the above-mentioned polymerizable groups in a molecule (polymerizable groups in the later-described polymerizable monomers should be all construed similarly to this).

The polymerizable monomer (a1) containing an acidic group in a molecule has an acidic group, such as a carboxylic acid group, a phosphoric acid group, a thiophosphoric acid group, a sulfonic acid group or a sulfinic acid group, and these acidic groups may be introduced singly or in combination.

Of the polymerizable monomers employable as the polymerizable monomers (a1) containing an acidic group in a molecule, examples of the polymerizable monomers having at least one carboxyl group in a molecule include monocarboxylic acids, dicarboxylic acids, tricarboxylic acids, tetracarboxylic acids, and derivatives of these acids. Examples of them include (meth)acrylic acid, maleic acid, p-vinylbenzoic acid, 11-(meth)acryloyloxy-1,1-undecanedicarboxylic acid (in the case of methacrylate: MAC10), 1,4-di(meth)acryloyloxyethylpyromellitic acid, 6-(meth)acryloyloxyethylnaphthalene-1,2,6-tricarboxylic acid, 4-(meth)acryloyloxymethyltrimellitic acid and its anhydride, 4-(meth) acryloyloxyethyltrimellitic acid (in the case of methacrylate: 4-MET) and its anhydride (in the case of methacrylate: 4-META), 4-(meth)acryloyloxybutyltrimellitic acid and its anhydride, 4-[2-hydroxy-3-(meth)acryloyloxy]butyltrimellitic acid and its anhydride, 2,3-bis(3,4-dicarboxybenzoyloxy)propyl(meth)acrylate, N, O-di(meth)acryloyloxytyrosine, O-(meth)acryloyloxytyrosine, N-(meth) acryloyloxytyrosine, N-(meth)acryloyloxyphenylalanine, N-(meth)acryloyl-p-aminobenzoic acid, N-(meth)acryloyl-O-aminobenzoic acid, N-(meth)acryloyl-5-aminosalicylic acid (in the case of methacrylate: 5-MASA), N-(meth)acryloyl-4-aminosalicylic acid, 2- or 3- or 4-(meth)acryloyloxybenzoic acid, an addition product of 2-hydroxyethyl(meth) acrylate with pyromellitic dianhydride (in the case of methacrylate: PMDM), an addition reaction product of 2-hydroxyethyl(meth)acrylate with maleic anhydride or 3,3',4,4'-benzophenonetetracarboxcylic dianhydride (in the case of methacrylate: BTDA) or 3,3',4,4'-biphenyltetracarboxylic dianhydride, 2-(3,4-dicarboxybenzoyloxy)-1,3-di(meth) acryloyloxypropane, an adduct of N-phenylglycine or N-tolylglycine with glycidyl (meth)acrylate, 4-[(2-hydroxy-3-(meth)acryloyloxypropyl)amino]phthalic acid, and 3- or 4-[N-methyl-N-(2-hydroxy-3-(meth)acryloyloxypropyl) amino]phthalic acid. These monomers can be used singly or in combination.

Of these acidic group-containing polymerizable monomers (a1), MAC-10, 4-MET, 4-META and 5-MASA are preferably used in the invention. These carboxyl group-containing polymerizable monomers can be used singly or in combination.

Examples of the polymerizable monomers having at least one phosphoric acid group in a molecule, which are used as the acidic group-containing polymerizable monomers (a1) in the invention, include 2-(meth)acryloyloxyethyl acid phosphate, 2- or 3-(meth)acryloyloxypropyl acid phosphate, 4-(meth)acryloyloxybutyl acid phosphate, 6-(meth)acryloyloxyhexyl acid phosphate, 8-(meth)acryloyloxyoctyl acid phosphate, 10-(meth)acryloyloxydecyl acid phosphate, 12-(meth)acryloyloxydodecyl acid phosphate, bis{2-(meth) acryloyloxyethyl}acid phosphate, bis{2- or 3-(meth) acryloyloxypropyl}acid phosphate, 2-(meth) acryloyloxyethylphenyl acid phosphate and 2-(meth) acryloyloxyethyl-p-methoxyphenyl acid phosphate. The phosphoric acid group in these compounds can be replaced with a thiophosphoric acid group. These polymerizable monomers having a phosphoric acid group can be used singly or in combination. In the present invention, 2-(meth)acryloyloxyethylphenyl acid phosphate and 10-(meth)acryloyloxydecyl acid phosphate are preferably used.

Of the polymerizable monomers employable as the acidic group-containing polymerizable monomers (a1) in the invention, examples of the polymerizable monomers having at least one sulfonic acid group in a molecule include 2-sulfoethyl(meth)acrylate, 2-sulfo-1-propyl(meth)acrylate, 1-sulfo-2-propyl(meth)acrylate, 1-sulfo-2-butyl(meth)acrylate, 3-sulfo-2-butyl(meth)acrylate, 3-bromo-2-sulfo-2-propyl(meth)acrylate, 3-methoxy-1-sulfo-2-propyl(meth)acrylate and 1,1-dimethyl-2-sulfoethyl(meth)acrylamide. These polymerizable monomers having a sulfonic acid group can be used singly or in combination. Of these, 2-methyl-2-(meth) acrylamidopropanesulfonic acid is preferably used.

In the present invention, the polymerizable monomer (a) is contained in an amount of usually 80 to 99.99% by weight, preferably 85 to 99.9% by weight, more preferably 90 to 99.5% by weight, in the weakly acidic to alkaline composition (I) excluding a filler. If the amount of the polymerizable monomer (a) is less than the lower limit of the above range, a cured product is not obtained or becomes brittle, or the curing time is markedly short frequently. If the amount thereof is more than the upper limit of the above range, the time required for curing becomes markedly long.

The polymerizable monomer (a) in the invention may be a polymerizable monomer wherein at least a part of acidic groups in such an acidic group-containing monomer (a1) as above are neutralized with alkali metal ions or alkaline earth metal ions.

It is particularly preferable to form a polymerizable monomer calcium salt (a2) wherein an acidic group in a molecule forms a calcium salt by virtue of a calcium ion that is an alkaline earth metal ion.

Such a polymerizable monomer calcium salt (a2) has a function of slowly liberating calcium in an organism such as oral cavity to accelerate recalcification of the surrounding tissues.

The polymerizable monomer (a2) wherein an acidic group in a molecule forms a calcium salt, which is used in the invention, is a polymerizable monomer wherein an acidic group of the polymerizable monomer (a1) having a polymerizable group and at least one acidic group in a molecule has been neutralized with a calcium ion. As the acidic group, a carboxylic acid group and/or a phosphoric acid group can be mentioned.

In the present invention, it is desirable that the acidic group of the polymerizable monomer (a1) having an acidic group is substantially completely neutralized. The expression "substantially completely neutralized" means that the gram equivalent of the acid of the acidic group and the gram equivalent of calcium are substantially equalized to each other, and the gram equivalent of calcium may exceed the gram equivalent of the acidic group. The "gram equivalent" is a value obtained by multiplying the number of moles by the valence of an acid (or base). That is to say, the gram equivalent is the number of moles of $H^+$ (or $OH^-$) capable of being liberated by the neutralization of an acid (or base). When a weak acid such as carboxylic acid group or phosphoric acid group is neutralized with calcium that is strongly basic, the pH value does not become 7 and tends to the alkaline side even if the weak acid is strictly completely neutralized.

In the present invention, the ratio (calcium base gram equivalent/acid gram equivalent) of the calcium base gram equivalent attributable to the calcium salt of the acidic group in a dental material or a dental composition to the acid gram equivalent of the acidic group is adjusted in the range of preferably 0.5 to 2.0 [gram equivalent/gram equivalent], more preferably 0.7 to 1.5 [gram equivalent/gram equivalent], still more preferably 0.8 to 1.2 [gram equivalent/gram equivalent]. If the ratio is less than the lower limit of the above range, the amount of the calcium component liberated is decreased, and contribution to the recalcification sometimes becomes substantially impossible. On the other hand, if the ratio is more than the upper limit of the above range, the alkali component becomes excessive and sometimes exerts evil influence on the properties of the dental material formed by curing.

As described above, the polymerizable monomer (a2) wherein the acidic group in a molecule forms a calcium salt is a polymerizable monomer wherein the acidic group present in the polymerizable monomer (a1) having an acidic group has been substantially completely neutralized, and this calcium may be a calcium salt obtained by previously neutralizing the polymerizable monomer (a1) having an acidic group, or may be calcium from a calcareous substance present in the circumference of the polymerizable monomer (a1) having an acidic group.

Such a calcium salt of the polymerizable monomer (a1) having an acidic group can be usually prepared by allowing a calcium compound such as $Ca(OH)_2$ and the polymerizable monomer (a1) having an acidic group to react with each other in substantially the same gram equivalents. The mode of this neutralization reaction has only to be a reaction mode in which the polymerizable monomer (a1) having an acidic group and the calcium compound can react with each other, and in usual, the calcium salt can be prepared by allowing them to react with each other in the presence of an aqueous medium such as water and then properly removing the reaction solvent by, for example, distillation, filtration or film separation after the reaction. The calcium salt thus prepared is preferably used after washing it with water or an aqueous medium, e.g., a lower alcohol such as ethanol. In the case where the calcium salt is used after washing as above, it is preferable to use the calcium salt after the solvent used for the washing is positively removed.

The content of the calcium salt contained in the thus purified product is in the range of preferably 40 to 100%, more preferably 60 to 100%, still more preferably 80 to 100%. The component other than the calcium salt contained in such a product is usually water or an aqueous medium having been used as a reaction solvent in the reaction, and the content of such a component other than the calcium salt is in the range of preferably 0 to 5%, more preferably 0 to 4%, still more preferably 0 to 2%. By producing the calcium salt in the above manner, the amount of a calcium compound liberated is decreased, and the pH value of the composition hardly tends to strong alkalinity.

If the calcium salt is prepared with properly controlling the pH value, loss of calcium during the reaction is extremely small, and therefore, the amounts charged can be regarded as composition (acid-base gram equivalent ratio) of the product. If necessary, the pH value of the solvent or the wash liquid having been removed or the pH value of the product may be measured and confirmed.

In the weakly acidic to alkaline composition (I) for use in the invention, a reducing compound (c) may be contained. However, in the concept of this reducing compound (c), the aforesaid compound (b) represented by the formula (1) is not included.

Examples of the reducing compounds (c) include an organic sulfinic acid-based compound (c11), a barbituric acid-based compound (c12), a compound having a 6-membered ring structure and an aromatic ring-based compound.

In the present invention, the organic sulfinic acid-based compound (c11) used as the reducing compound (c) is, for example, an organic sulfinic acid or its salt. More specific examples of the organic sulfinic acid-based compounds (c11) include sulfinic acid, and alkali metal salts, alkaline earth metal salts, amine salts or ammonium salts of sulfinic acid.

By particularly using an aromatic sulfinate in the invention, a color tone of a cured product becomes excellent.

Examples of the alkali metal salts include lithium salt, sodium salt and potassium salt of the above compound. Examples of the alkaline earth metal salts include magnesium salt, calcium salt, strontium salt and barium salt. Examples of the amine salts include:

salts of primary amines such as methylamine, ethylamine, propylamine, butylamine, aniline, toluidine, phenylenediamine and xylylenediamine;

salts of secondary amines such as dimethylamine, diethylamine, dipropylamine, dibutylamine, piperidine, N-methylaniline, N-ethylaniline, diphenylamine and N-methyltoluidine; and salts of tertiary amines such as trimethylamine, triethylamine, pyridine, N,N-dimethylaniline, N,N-di(β-hydroxyethyl)aniline, aniline, N,N-dimethyltoluidine, N,N-diethyltoluidine and N,N-(β-hydroxyethyl)toluidine.

Examples of the salts of ammonium compounds include ammonium salt, tetramethylammonium salt, tetraethylammonium salt, tetrapropylammonium salt and trimethylbenzylammonium salt.

Examples of the organic sulfinic acids include alkanesulfinic acids, such as ethanesulfinic acid, propanesulfinic acid, hexanesulfinic acid, octanesulfinic acid, decanesulfinic acid and dodecanesulfinic acid; alicyclic sulfinic acids, such as cyclohexanesulfinic acid and cyclooctanesulfinic acid; and aromatic sulfinic acids, such as benzenesulfinic acid, o-toluenesulfinic acid, p-toluenesulfinic acid, ethylbenzenesulfinic acid, decylbenzenesulfinic acid, dodecylbenzenesulfinic acid, chlorobenzenesulfinic acid and naphthalenesulfinic acid.

Examples of organic sulfinates include lithium benzenesulfinate, sodium benzenesulfinate, potassium benzenesulfinate, magnesium benzenesulfinate, calcium benzenesulfinate, strontium benzenesulfinate, barium benzenesulfinate, butylamine benzenesulfinate, aniline benzenesulfinate, toluidine benzenesulfinate, phenylenediamine benzenesulfinate, diethylamine benzenesulfinate, diphenylamine benzenesulfinate, triethylamine benzenesulfinate, ammonium benzenesulfinate, tetramethylammonium benzenesulfinate, trimethylbenzylammonium benzenesulfinate, lithium o-toluenesulfinate, sodium o-toluenesulfinate, potassium o-toluenesulfinate, calcium o-toluenesulfinate, cyclohexylamine o-toluenesulfinate, aniline o-toluenesulfinate, ammonium o-toluenesulfinate, tetraethylammonium o-toluenesulfinate, lithium p-toluenesulfinate, sodium p-toluenesulfinate, potassium p-toluenesulfinate, barium p-toluenesulfinate, ethylamine p-toluenesulfinate, toluidine p-toluenesulfinate, N-methylaniline p-toluenesulfinate, pyridine p-toluenesulfinate, ammonium p-toluenesulfinate, tetramethylammonium p-toluenesulfinate, sodium β-naphthalenesulfinate, strontium β-naphthalenesulfinate, triethylamine β-naphthalenesulfinate, N-methyltoluidine β-naphthalenesulfinate, ammonium β-naphthalenesulfinate and trimethylbenzylammonium β-naphthalenesulfinate.

In the present invention, the organic sulfinic acid-based compound (c11) is used in an amount of usually 0.05 to 20 parts by weight, preferably 0.1 to 18 parts by weight, more preferably 0.5 to 15 parts by weight, in 100 parts by weight of the total amount of the polymerizable monomer (a) and other components except a filler contained in the weakly acidic to alkaline composition (I). If the amount of this compound used is too small, discoloration of a cured product easily takes place, and if the amount thereof is too large, curability tends to be lowered.

Examples of the barbituric acid-based compounds (c12) which can be added to the weakly acidic to alkaline composition (I) for use in the invention together with the organic sulfinic acid-based compound (c11) or separately from the organic sulfinic acid-based compound (c11) include 1,3,5-trimethylbarbituric acid, 1,3,5-triethylbarbituric acid, 1,3-dimethyl-5-ethylbarbituric acid, 1,5-dimethylbarbituric acid, 1-methyl-5-ethylbarbituric acid, 1-methyl-5-propylbarbituric acid, 5-ethylbarbituric acid, 5-propylbarbituric acid, 5-butylbarbituric acid, 5-methyl-1-butylbarbituric acid, 1-benzyl-5-phenylbarbituric acid, 1-cyclohexyl-5-ethylbarbituric acid, and alkali metal salts of these acids.

The amount of the barbituric acid-based compound (c12) which can be added to the weakly acidic to alkaline composition (I) for use in the invention is in the range of usually 0.1 to 10 parts by weight, preferably 0.3 to 8 parts by weight, more preferably 0.5 to 5 parts by weight, in 100 parts by weight of the total amount of the polymerizable monomer (a) and other components except a filler contained in the weakly acidic to alkaline composition (I). If the amount of this compound used is too small, discoloration of a cured product easily takes place, and if the amount thereof is too large, curability tends to be lowered.

In the weakly acidic to alkaline composition (I) for use in the invention, the organic sulfinic acid-based compound (c11) and the barbituric acid-based compound (c12) can be used in combination, and in this case, their blending ratio [(c11)/(c12)] is in the range of 0.1 to 100, preferably 0.05 to 50, more preferably 0.1 to 10.

In the present invention, an organic reducing compound can be added to the composition (I). Examples of the organic reducing compounds employable herein include aromatic amines, such as N,N-dimethylaniline, N,N-dimethyl-p-toluidine (DMPT), N,N-diethyl-p-toluidine, N,N-diethanol-p-toluidine (DEPT), N,N-dimethyl-p-tert-butylaniline, N,N-dimethylanisidine, N,N-dimethyl-p-chloroaniline, N,N-dimethylaminoethyl (meth)acrylate, N,N-diethylaminoethyl (meth)acrylate, N,N-dimethylaminobenzoic acid and its alkyl ester, N,N-diethylaminobenzoic acid (DEABA) and its alkyl ester, and N,N-dimethylaminobenzaldehyde (DMABAd). Of these, DMPT, DEPT, DEABA or DMABAd can be preferably used as the organic reducing compound in the invention.

In the present invention, such an organic reducing compound as above is used in an amount of usually 0.1 to 10 parts by weight, preferably 0.3 to 8 parts by weight, more preferably 0.5 to 7 parts by weight, in 100 parts by weight of the total amount of the polymerizable monomer (a) and other components except a filler contained in the composition (I), or is used in an amount of usually 0.001 to 10% by weight, preferably 0.002 to 5% by weight, more preferably 0.003 to 3% by weight, based on 100% by weight of the total amount of the photopolymerization initiator (c2) and the peroxide (c3). By the use of the organic reducing compound in the above amount, polymerization proceeds smoothly, and problems of coloring of the composition, embrittlement of the reaction cured product, etc. are not brought about.

The weakly acidic to alkaline composition (I) for use in the invention is a composition comprising the polymerizable monomer (a) and the compound represented by the formula (1), and the pH value of the composition is in the range of usually 4.5 to 14, preferably 4.5 to 12, particularly preferably 4.5 to 9. If the pH value is less than the lower limit of the above range, hydrolysis reaction of the polymerizable monomer (a) or the compound represented by the formula (1) contained in the composition (I) is liable to proceed, and it tends to become difficult to stably keep the polymerizable monomer (a) or the compound represented by the formula (1). If the pH value exceeds the upper limit of the above range, partial polymerization reaction or curing reaction of the polymerizable monomer (a) contained in the composition (I) is liable to occur, and storage stability of the composition (I) tends to be impaired.

In order to maintain the pH value of the weakly acidic to alkaline composition (I) in the above range, the polymerizable monomer (a) and the compound represented by the formula (1) are used in combination to adjust the pH value of the composition (I) as above. When the polymerizable monomer (a1) having an acidic group is used in this case, this monomer is not used as it is but is substantially completely neutralized with an alkali metal such as sodium or potassium or an alkaline earth metal such as calcium prior to use. Further, a basic compound such as amine is added to neutralize the acidic group, and thereby, the pH value of the composition (I) is adjusted to a value in the above range. In the present invention, the pH value is a value measured at 23° C.

For example, in the case where hydroxyethyl methacrylate (HEMA) and a sodium salt (NPG-Na) of the compound represented by the formula (1) are used in combination, the pH value of the resulting composition (I) at 23° C. can be adjusted to 6.5 by blending them in a quantity ratio of 95:5 (HEMA:NPG-Na). In the case where triethylene glycol dimethacrylate (TEGDMA) and a sodium salt (NPG-Na) of the compound represented by the formula (1) are used in combination, the pH value of the resulting composition (I) at 23° C. can be adjusted to 4.5 by blending them in a quantity ratio of 95:5 (TEGDMA:NPG-Na). Further, by blending TEGDMA, NPG-Na and N,N-dimethyl-p-toluidine (DMPT) in a weight ratio of 96.5:3:0.5, the pH value of the composition (I) can be adjusted to 4.5, and by blending TEGDMA, NPG-Na and sodium p-toluenesulfonate (p-TSNa) in a weight ratio of 40:3:6, the pH value of the composition (I) can be adjusted to 6.5.

To the weakly acidic to alkaline composition (I) for use in the invention, a filler (d) may be added.

As the fillers employable in the invention, an organic filler, an inorganic filler and an organic composite filler can be mentioned, and these fillers can be used singly or in combination.

Examples of the organic fillers for use in the invention include a powder polymer filler obtained by pulverization of a polymer or dispersion polymerization and a filler obtained by polymerizing a polymerizable monomer containing a crosslinking agent and then pulverizing the resulting polymer. The polymerizable monomer employable as a raw material of the filler is not specifically restricted, but the polymerizable monomers previously given as examples of the polymerizable monomers (a) are employable, and they can be used singly to form homopolymers or can be used in combination to form copolymers. By adding a crosslinking agent, crosslinked (co)polymers can be formed.

Examples of the crosslinking agents employable in the invention include polymethyl methacrylate (PMMA), polyethyl methacrylate, polypropylmethacrylate, polybutylmethacrylate (PBMA), polyvinyl acetate (PVAc), polyethylene glycol (PEG), polypropylene glycol (PPG) and polyvinyl alcohol (PVA).

In the case where an inorganic filler is used as the filler (d) in the invention, examples of the inorganic fillers include silica, silica alumina, alumina, alumina quartz, glasses including barium glass and strontium glass, titania, zirconia, calcium carbonate, kaolin, clay, mica, aluminum sulfate, barium sulfate, calcium sulfate, titanium oxide and calcium phosphate.

In the present invention, an organic composite filler is also employable as the filler (d). The organic composite filler used herein is a filler obtained by coating the surface of the above-mentioned inorganic filler with a polymer of a polymerizable monomer and then pulverizing the thus treated filler. An example of such an organic composite filler is a filler (TMPT.f) obtained by polymerization-coating finely powdered silica or zirconium oxide of the aforesaid inorganic fillers with a polymerizable monomer containing trimethylolpropane tri(meth)acrylate (TMPT) as a main component and pulverizing the resulting polymer.

When the filler (d) is added to the weakly acidic to alkaline composition (I) for use in the invention, the filler (d) is used in an amount of usually 10 to 80% by weight, preferably 15 to 70% by weight, more preferably 20 to 60% by weight, in the total amount (100% by weight) of the composition (I). If the amount of the filler is less than the lower limit of the above range, the working-effect due to use of the filler (d), particularly an effect of improving fluidity, is hardly exhibited. If the filler is used in an amount exceeding the upper limit of the above range, viscosity of the weakly acidic to alkaline composition (I) becomes too high, so that the workability is lowered, and besides, effective bond strength is not exhibited.

In the present invention, the filler can be added to the composition (I), but the pH value of the composition (I) is not changed even if such a filler is added. Hence, the pH value of the composition does not vary depending upon the presence of the filler.

By combining the components, the pH value of the weakly acidic to alkaline composition (I) at 23° C. can be set in the aforesaid range, and thereby, the polymerizable monomer (a) contained in the weakly acidic to alkaline composition (I) can be stably kept for a long period of time.

When the acidic group-containing polymerizable monomer is used in the invention without substantially using a polymerizable monomer having a strongly acidic group in order to maintain the pH value of the weakly acidic to alkaline composition (I) in the aforesaid range, the acidic group-containing polymerizable monomer is used in the form of a metal salt by using an alkali metal such as sodium or potassium. Further, the pH value of the weakly acidic to alkaline composition (I) is adjusted by adding a basic compound such as an amine or adding a weakly acidic to alkaline adjustor, preferably a neutral to alkaline adjustor, to the composition (I). By adjusting the pH value of the composition (I) as above, the polymerizable monomer (a) assumes a state of stable liquid or paste. Even if the polymerizable monomer (a) is in this state, this monomer has excellent room temperature storage property, and the composition (I) of the invention that is in a mixed state of the components is stable at 23° C. for usually not shorter than 3 months, preferably not shorter than 12 months, more preferably not shorter than 24 months, and is stable at 76° C. for usually not shorter than 1 hour, preferably not shorter than 4 hours, more preferably not shorter than 8 hours. That is to say, by adjusting the pH value of the weakly acidic to alkaline composition (I) for use in the invention as above, the weakly acidic to alkaline composition (I) does not vary to a substantially unusable state such as a gelatinized or viscosity-increased state. When this composition (I) having excellent storage stability is applied to a tooth substance as a dental adhesive or a sealant after it is exposed to such conditions as above, it exhibits a tensile strength of not less than 4 MPa to bovine dentin and exhibits gap inhibition of not less than 70% in the sealing test.

The strongly acidic composition (II) for use in the invention is a composition containing the aforesaid polymerizable monomer (a), and has a pH value at 23° C. of usually not less than 0.1 but less than 4.5, preferably 0.5 to 4, more preferably 1 to 3.5. If the pH value is less than the lower limit of the above range, strong irritation is sometimes given to oral mucosa such as gum that is an organism, and such a composition is unsuitable for, for example, an adhesive for dental use. If the pH value is more than the upper limit of the above range, lowering of bond performance and sealing performance is induced.

In order that the pH value of the strongly acidic composition (II) for use in the invention at 23° C. may be set in the above range, incorporation of the polymerizable monomer (a1) containing an acidic group as the polymerizable monomer (a) or addition of an acidic adjustor is adoptable.

To the strongly acidic composition (II), a photopolymerization initiator or a peroxide-based polymerization initiator can be added.

The photopolymerization initiator (c2) used herein plays a role of curing the curable composition of the invention by being excited by light singly or in the presence of another compound. For example, an α-ketocarbonyl compound (c21) or an acylphosphine oxide compound (c22) can be mentioned. Examples of the α-ketocarbonyl compounds, i.e., components (c21) of the invention, include α-diketone, α-ketoaldehyde, α-ketocarboxylic acid and α-ketocarboxylic acid ester. Specific examples of the α-ketocarbonyl compounds (c21) include α-diketones, such as diacetyl, 2,3-pentadione, 2,3-hexadione, benzil, 4,4'-dimethoxybenzil, 4,4'-diethoxybenzil, 4,4'-oxybenzil, 4,4'-dichlorobenzil, 4-nitrobenzil, α-naphthil, β-naphthil, camphorquinone (CQ), camphorquinonesulfonic acid, camphorquinonecarboxylic acid and 1,2-cyclohexanedione; α-ketoaldehydes, such as methylglyoxal and phenylglyoxal; pyruvic acid, benzoylformic acid, phenylpyruvic acid, methyl pyruvate, ethyl benzoylfomate, methyl phenylpyruvate and butyl phenylpyruvate. Of these α-ketocarbonyl compounds (c21), α-diketones are preferably used from the viewpoint of stability, etc. Of the α-diketones, diacetyl, benzil and camphorquinone (CQ) are preferable.

Examples of the acylphosphine oxide compounds (c22) used as the photopolymerization initiators (c2) include benzoyldimethoxyphosphine oxide, benzoylethoxyphenylphosphine oxide, benzoyldiphenylphospine oxide, 2-methylbenzoyldiphenylphosphine oxide and 2,4,6-trimethylbenzoyldiphenylphosphine oxide. The α-ketocarbonyl compounds (c21) and the acylphosphine oxide compounds (c22) can be used singly or in combination.

Such a photopolymerization initiator (c2) is used in an amount of usually 0.001 to 10% by weight, preferably 0.002 to 5% by weight, more preferably 0.003 to 3% by weight, in 100% by weight of the total amount of the polymerizable monomer (a) and other components except the filler (d) contained in the strongly acidic composition (II). If the amount of the photopolymerization initiator (c2) is less than the lower limit of the above range, polymerization reaction does not proceed occasionally, and if the amount thereof is more than the upper limit of the above range, discoloration of a cured product is brought about, and the resulting cured product becomes brittle.

To the strongly acidic composition (II) of the invention, a peroxide-based polymerization initiator (c3) can be added.

As the peroxide-based polymerization initiators (c3) added to the strongly acidic composition (II) for use in the invention, organic peroxides and inorganic peroxides can be mentioned, and any of these peroxides is employable in the invention.

Examples of the organic peroxides used as the peroxide-based polymerization initiators (c3) in the strongly acidic composition (II) of the invention include diacetyl peroxide, dipropyl peroxide, dibutyl peroxide, dicapryl peroxide, dilauryl peroxide, benzoyl peroxide (BPO), p,p'-dichlorobenzoyl peroxide, p,p'-dimethoxybenzoyl peroxide, p,p'-dimethylbenzoyl peroxide and p,p'-dinitrodibenzoylperoxide. Examples of the inorganic peroxides used as the inorganic peroxide-based polymerization initiators (c3) include ammonium persulfate, potassium persulfate, potassium chlorate, potassium bromate and potassium perphosphate. These compounds can be used singly or in combination.

Such a peroxide-based polymerization initiator (c3) is used in an amount of usually 0.1 to 10% by weight, preferably 0.3 to 8% by weight, more preferably 0.5 to 7% by weight, in 100% by weight of the total amount of the polymerizable monomer (a) and other components except a filler contained in the strongly acidic composition (II). If the amount of the peroxide-based initiator (c3) is less than the lower limit of the above range, the polymerization curing time sometimes becomes markedly long, or the composition is not cured occasionally. If the amount thereof is more than the upper limit of the above range, curing is markedly accelerated, and a sufficient pot life cannot be ensured.

The reaction-curable adhesive composition (IV) exhibiting acidity of the invention is a composition (IV) comprising the weakly acidic to alkaline composition (I) and the strongly acidic composition (II), and this composition (IV) is an adhesive composition having reaction curability and exhibiting acidity.

The reaction-curable adhesive composition (IV) exhibiting acidity can be prepared by blending the weakly acidic to alkaline composition (I) with the strongly acidic composition (II) so that the pH value of a mixture of the composition (I) and the composition (II) as measured at 23° C. may become usually 0.5 to 1, preferably 1 to 5, more preferably 1.4 to 4.5.

That is to say, by mixing the weakly acidic to alkaline composition (I) with the strongly acidic composition (II) so that the pH value of the resulting composition (IV) at 23° C. may become a value of the above range, the mixture (IV), namely the reaction-curable composition (IV) exhibiting acidity of the invention, has excellent bond property to teeth and the like, and besides, the photopolymerization initiator (c1) or the peroxide-based polymerization initiator (c2) contained in the strongly acidic to alkaline composition (II) and the compound represented by the formula (1) contained in the weakly acidic composition (I) are brought into contact with each other, whereby the composition (IV) comes to exhibit reaction curability according to the type of the polymerization initiator used.

Although the weakly acidic to alkaline composition (I) and the strongly acidic composition (II) are blended so that the resulting composition may have a value of the above range, the composition (I) and the composition (II) are used in a weight ratio of usually 1:0.5 to 1:10, preferably 1:1 to 1:6.

When the polymerization initiator contained in the strongly acidic composition (II) is, for example, a photopolymerization initiator, the reaction-curable adhesive composition (IV) exhibiting acidity of the invention shows photopolymerizability, and when the polymerization initiator contained in the strongly acidic composition (II) is a peroxide-based polymerization initiator, the composition (IV) shows room temperature or thermal curability. Particularly when a peroxide-based polymerization initiator is used, a pot life or a curing time of the composition (IV) can be properly determined by this peroxide-based polymerization initiator added.

Further, since the pH of the composition (IV) is on the acidic side before curing, the composition (IV) exhibits extremely high bond strength to teeth and the like.

Furthermore, by adding a filler to any one or both of the weakly acidic to alkaline composition (I) and the strongly acidic composition (II), high bond property and sealing property are exhibited. Moreover, by controlling the amount of the filler added, it becomes possible to control the viscosity of the composition (IV), and a viscosity suitable for the treatment of teeth and the like can be obtained.

Such weakly acidic to alkaline composition (I) and strongly acidic composition (II) as above are usually packaged separately so that they may not come into contact with each other. Especially when the photopolymerization initiator (c1) is contained in the strongly acidic composition (II), a light-shielding container is used as at least the container to contain the strongly acidic composition (II).

The present invention comprises the weakly acidic to alkaline composition (I) and the strongly acidic composition (II) which are packaged separately. However, by combining a primer composition (III) with them, they can be preferably used as a dental adhesive kit.

The dental adhesive kit of the invention is a dental adhesive kit comprising:

a weakly acidic to alkaline composition (I) comprising (a) a polymerizable monomer and (b) a compound represented by the following formula (1):

$$R^1-C_6H_4-NR^2CH_2COOR^3 \qquad (1)$$

wherein $R^1$ and $R^2$ are each independently a hydrogen atom or an alkyl group which may have a functional group, and $R^3$ is a hydrogen atom or a metal atom, a strongly acidic composition (II) comprising (a) a polymerizable monomer, and a primer composition (III), wherein the primer composition (III) is formed from:
(a) a polymerizable monomer,
(e) an aromatic tertiary amine, and
(f) a water-soluble solvent.

In this dental adhesive kit, the weakly acidic to alkaline composition (I), the strongly acidic composition (II) and the primer composition (III) are packaged separately.

As the weakly acidic to alkaline composition (I) and the strongly acidic composition (II) to constitute the dental adhesive kit of the invention, the weakly acidic to alkaline composition (I) and the strongly acidic composition (II) described above are used.

The primer composition (III) to constitute the dental adhesive kit of the invention contains:
(a) a polymerizable monomer,
(e) an aromatic tertiary amine, and
(f) in a water-soluble solvent.

As the polymerizable monomer (a), the polymerizable monomer (a) described above for the weakly acidic to alkaline composition (I) is employable.

Examples of the aromatic tertiary amines (e) to form the primer composition (III) for use in the invention include aromatic amines, such as N,N-dimethylaniline, N,N-dimethyl-p-toluidine (DMPT), N,N-diethyl-p-toluidine, N,N-diethanol-p-toluidine (DEPT), N,N-dimethyl-p-tert-butylaniline, N,N-dimethylanisidine, N,N-dimethyl-p-chloroaniline, N,N-dimethylaminoethyl (meth)acrylate, N,N-diethylaminoethyl(meth)acrylate, N,N-dimethylaminobenzoic acid and its alkyl ester, N,N-diethylaminobenzoic acid (DEABA) and its alkyl ester, and N,N-dimethylaminobenzaldehyde (DMABAd). Of these, DMPT, DEPT, DEABA and DMABAd can be preferably used.

Such an aromatic tertiary amine (e) is used in an amount of usually 0.01 to 10% by weight, preferably 0.05 to 7% by weight, more preferably 0.1 to 5% by weight, in the total amount of the primer composition (III). By the use of the aromatic tertiary amine (e) in the above amount, excellent bond property is exhibited, and discoloration of a cured product does not take place. That is to say, if the amount of the aromatic tertiary amine (e) used is more than the upper limit of the above range, the primer composition (III) is sometimes discolored during storage, and the adhesive interface and its vicinity are sometimes discolored.

In the primer composition (III) for use in the invention, a water-soluble solvent (f) is further contained. The water-soluble solvent (f) used herein is water, a hydrophilic organic solvent or a water-containing hydrophilic organic solvent. The hydrophilic organic solvent is an organic solvent to homogeneously dissolve or disperse the polymerizable monomer (a) and the aromatic tertiary amine (e) contained in the primer composition (III), and is desirably an organic solvent capable of being mixed with water in any proportion. Examples of such hydrophilic organic solvents include alcohols, such as methanol, ethanol (EtOH) and propanol; ketones, such as acetone and methyl ethyl ketone; ethers, such as tetrahydrofuran (THF); and amides, such as N,N-dimethylformamide. Of these hydrophilic organic solvents, ethanol and acetone are preferable taking into account toxicity and irritation given to the dental pulp.

As the water-soluble solvent (f) for use in the primer composition (III) in the invention, water is also employable. Water employable as the water-soluble solvent (f) is, for example, distilled water, ion-exchanged water or an isotonic sodium chloride solution. In the present invention, distilled water or ion-exchanged water is particularly preferably used. As described above, water or the hydrophilic organic solvent is employable as the aqueous solvent for use in the invention, and the hydrophilic organic solvent can also contain water, so that a water-containing hydrophilic organic solvent that is a mixture of water and the aqueous organic solvent is also employable as the aqueous solvent (f) in the invention.

In the primer composition (III) for use in the invention, such an aqueous medium (f) as above is used in an amount of usually 10 to 90% by weight, preferably 15 to 80% by weight, more preferably 20 to 70% by weight. By setting the amount of the aqueous solvent in the above range, a proper amount of the aqueous solvent remains on, for example, a tooth substance surface, and therefore, very excellent bond performance is exhibited.

It has been described above that a polymerization initiator other than the compound represented by the formula (1), which is the polymerization initiator (c), is added to the strongly acidic to alkaline composition (II), but in the case where mixing of the peroxide-based polymerization initiator (c3) is carried out in a state of liquid or paste, room temperature storage property cannot be sufficiently ensured occasionally. When the polymerization initiator (c) is a polymerization initiator other than the peroxide-based polymerization initiator (c3), sufficient storage stability can be ensured at room temperature even if the polymerization initiator and the polymerizable monomer are brought into contact with each other. Therefore, the polymerization initiator (c) does not need to be always added to the composition (II), and it may be added to other compositions. However, when the polymerization initiator (c) is the peroxide-based polymerization initiator (c3), polymerization reaction sometimes proceeds before using even if the peroxide-based polymerization initiator (c3) is added to the composition (I), and therefore, the peroxide-based polymerization initiator (c3) is desired to be packaged so as not to be in contact with other components.

In the present invention, a polymerization initiator other than the component (b) can be contained as the component (c) in the composition (II).

As described hereinbefore, the composition (I) of the invention is a weakly acidic to alkaline composition, and the composition (II) is a strongly acidic composition. In the present invention, these weakly acidic to alkaline composition (I) and strongly acidic composition (II), and if necessary, the primer composition (III) are packaged independently to form a dental adhesive kit. Although the weakly acidic to alkaline composition (I) and the strongly acidic composition (II) are generally used by kneading them, the primer composition (III) is generally directly supplied to a surface of a tooth for the treatment, to form a primer layer.

By the use of such a dental adhesive kit or the reaction-curable adhesive composition (IV), very excellent bond property to a tooth substance or the like is exhibited.

It is preferable to use the reaction-curable adhesive composition or the dental adhesive kit of the invention for a tooth surface after the tooth surface is treated with a self-etching primer composition (V) which contains (A) a polymerizable monomer, (B) a reducing inorganic compound containing sulfur, (C) a ketone-based solvent and (D) water, does not substantially contain an alcohol-based solvent and has storage stability of not shorter than 2 hours at 65° C.

The self-etching primer composition (V) is a composition which contains (A) a polymerizable monomer, (B) a reducing inorganic compound containing sulfur, (C) a ketone-based solvent and (D) water and does not substantially contain a lower alcohol such as ethanol.

In the present invention, it is preferable to use the reaction-curable adhesive composition of the invention after the self-etching primer composition (V) is directly applied to a tooth substance surface which has been previously abraded.

The polymerizable monomer (A) used as a component to constitute the self-etching primer composition (V) is, for example, a compound having a radical-polymerizable unsaturated group, such as acryloyl group, methacryloyl group (acryloyl group and methacryloyl group being sometimes referred to as "(meth)acryloyl group" generically), styryl group, vinyl group or allyl group. The polymerizable monomer (A) used herein has only to have at least one unsaturated group in one molecule, and there can be used a polymerizable monomer having one unsaturated group (monofunctional monomer), a polymerizable monomer having two unsaturated groups (bifunctional monomer) or a polymerizable monomer having three unsaturated groups (trifunctional monomer). Such a polymerizable monomer may have a functional group, such as carboxyl group, phosphoric acid group, sulfonic acid group, hydroxyl group, amino group or glycidyl group, in a molecule.

Examples of the polymerizable monomers (A) include:

fatty acid esters of (meth)acrylic acid, such as methyl (meth)acrylate, ethyl(meth)acrylate, propyl(meth)acrylate, butyl (meth)acrylate, neopentyl glycol di(meth)acrylate and trimethylolpropane tri(meth)acrylate;

hydroxyl group-containing (meth)acrylates, such as 2-hydroxyethyl(meth)acrylate, 2- or 3-propyl(meth)acrylate, glycelol mono(meth)acrylate, diethylene glycol mono(meth) acrylate, triethylene glycol mono(meth)acrylate, pentaethylene glycol mono(meth)acrylate, 2-hydroxy-3-phenoxypropyl(meth)acrylate, and an adduct of 1 mol of bisphenol A with 2 mol of glycidyl(meth)acrylate;

hydroxyl group-containing (meth)acrylamides, such as methylol (meth)acrylamide;

polyethylene glycol di(meth)acrylates, such as ethylene glycol di(meth)acrylate, diethylene glycol di(meth)acrylate, triethylene glycol di(meth)acrylate, pentaethylene glycol di(meth)acrylate, nonaethylene glycol di(meth)acrylate and tetradecaethylene glycol di(meth)acrylate;

polypropylene glycol di(meth)acrylates, such as propylene glycol di(meth)acrylate, dipropylene glycol di(meth)acrylate, tripropylene glycol di(meth)acrylate and nonapropylene glycol di(meth)acrylate;

mono(meth)acrylates wherein any one of (meth)acrylate groups in the above-mentioned polyethylene glycol di(meth) acrylates and polypropylene glycol di(meth)acrylates is replaced with a methyl group or an ethyl group;

(meth)acrylates having a urethane bond, such as an adduct of 2-(meth)acryloyloxyethyl isocyanate or 2,2,4-trimethylhexamethylene diisocyanate or 1,3,5-trimethylhexamethylene diisocyanate with 2-hydroxyethyl (meth)acrylate; and 2,2-bis(4-(meth)acryloyloxypolyethoxyphenyl)propane obtained by further condensing an addition product of bisphenol A with oxyethylene, with (meth)acrylic acid.

These polymerizable monomers (A) can be used singly or in combination.

Examples of the components having at least one carboxyl group in one molecule, which can be used as the polymerizable monomers (A), include monocarboxylic acids, dicarboxylic acids, tricarboxylic acids, tetracarboxylic acids and derivatives of these acids. Specifically, there can be mentioned, for example, (meth)acrylic acid, maleic acid, p-vinylbenzoic acid, 11-(meth)acryloyloxy-1,1-undecanedicarboxylic acid (MAC-10), 1,4-di(meth)acryloyloxyethylpyromellitic acid, 6-(meth)acryloyloxyethylnaphthalene-1,2,6-tricarboxylic acid, 4-(meth)acryloyloxymethyltrimellitic acid and its anhydride, 4-(meth)acryloyloxyethyltrimellitic acid and its anhydride, 4-(meth)acryloyloxybutyltrimellitic acid and its anhydride, 4-[2-hydroxy-3-(meth)acryloyloxybutyl]trimellitic acid and its anhydride, 2,3-bid(3,4-dicarboxybenzoyloxy)propyl (meth)acrylate, N,O-di(meth)acryloyloxytyrosine, O-(meth)acryloyloxytyrosine, N-(meth)acryloyloxytyrosine, N-(meth)acryloyloxyphenylalanine, N-(meth)acryloyl-p-aminobenzoic acid, N-(meth)acryloyl-O-aminobenzoic acid, N-(meth)acryloyl-5-aminosalicylic acid, N-(meth)acryloyl-4-aminosalicylic acid, 2- or 3- or 4-(meth)acryloyloxybenzoic acid, an addition product (PMDM) of 2-hydroxyethyl (meth)acrylate with pyromellitic dianhydride, an addition reaction product of 2-hydroxyethyl(meth)acrylate with maleic anhydride or 3,3',4,4'-benzophenonetetracarboxcylic dianhydride (BTDA) or 3,3',4,4'-biphenyltetracarboxylic dianhydride, 2-(3,4-dicarboxybenzoyloxy)-1,3-di(meth) acryloyloxypropane, an adduct of N-phenylglycine or N-tolylglycine with glycidyl (meth)acrylate, 4-[(2-hydroxy-3-(meth)acryloyloxypropyl)amino]phthalic acid, and 3- or 4-[N-methyl-N-(2-hydroxy-3-(meth)acryloyloxypropyl) amino]phthalic acid. Of these, 11-(meth)acryloyloxy-1,1-undecanedicarboxylic acid (MAC-10), a 4-(meth)acryloyloxyalkyltrimellitic acid-based compound or its anhydride, such as 4-methacryloyloxyethyltrimellitic acid (4-MET), and N-methacryloyl-5-aminosalicylic acid (%-MASA) are preferably used. Of these, 4-methacryloyloxyethyltrimellitic acid (4-MET) is particularly preferably used, and by incorporating this 4-MET in an amount of not more than 20% by weight as at least a part of the polymerizable monomer (A), a composition having excellent heat stability is obtained. These polymerizable monomers (A) having a carboxyl group can be used singly or in combination.

Examples of the polymerizable monomers (A) having at least one phosphoric acid group in one molecule include 2-(meth)acryloyloxyethyl acid phosphate, 2- or 3-(meth)acryloyloxypropyl acid phosphate, 4-(meth)acryloyloxybutyl acid phosphate, 6-(meth)acryloyloxyhexyl acid phosphate, 8-(meth)acryloyloxyoctyl acid phosphate, 10-(meth)acryloyloxydecyl acid phosphate, 12-(meth)acryloyloxydodecyl acid phosphate, bis[(meth)acryloyloxyalkyl]acid phosphate-based compounds, such as bis[2-(meth)acryloyloxyethyl]acid phosphate and bis[2- or 3-(meth)acryloyloxypropyl]acid phosphate, 2-(meth)acryloyloxyethylphenyl acid phosphate, and 2-(meth)acryloyloxyethyl-p-methoxyphenyl acid phosphate.

The phosphoric acid group in these compounds may be replaced with a thiophosphoric acid group. Of the above compounds, 2-(meth)acryloyloxyethylphenyl acid phosphate and 10-(meth)acryloyloxydecyl acid phosphate are preferably used. These polymerizable monomers (A) having a phosphoric acid group can be used singly or in combination.

Examples of the polymerizable monomers (A) having at least one sulfonic acid group in one molecule include 2-sulfoethyl (meth)acrylate, 2- or 1-sulfo-1- or 2-propyl(meth) acrylate, 1- or 3-sulfo-2-butyl(meth)acrylate, 3-bromo-2- sulfo-2-propyl (meth)acrylate, 3-methoxy-1-sulfo-2-propyl (meth)acrylate and 1,1-dimethyl-2-sulfoethyl(meth)acrylamide.

Of these, 2-methyl-2-(meth)acrylamidopropanesulfonic acid is preferably used. These polymerizable monomers (A) having a sulfonic acid group can be used singly or in combination.

The above polymerizable monomers (A) can be used singly or in combination. When the polymerizable monomers (A) are used in combination, polymerizable monomers having an acidic group and/or an acid anhydride group are preferably used, and polymerizable monomers having at least one group selected from the group consisting of a carboxylic acid group, a phosphoric acid group and their acid anhydride groups are particularly preferable.

A carboxylic acid compound preferably used herein is an aromatic carboxylic acid compound, a dicarboxylic acid compound or a dicarboxylic acid compound adjacent to an aromatic ring. A phosphoric acid compound preferably used herein is an alkyl ester, particularly a dialkyl ester [R—O—PO(OH)—O—R' (wherein R and R' are each an alkyl group)].

In the present invention, a (meth)acrylic polmerizable monomer is particularly preferable as the polymerizable monomer (A). It is a matter of course that plural kinds of the polymerizable monomers can be used in combination in the invention. In the present invention, it is particularly preferable to use a (methy)acrylic polymerizable monomer having a carboxylic acid group and/or its acid anhydride group and a (meth)acrylic polymeriable monomer having a phosphoric acid group and/or its acid anhydride group in combination. Further, a combination of a 4-(meth)acryloyloxyalkyltrimellitic acid-based compound and/or its acid anhydride and a bis[(meth)acryloyloxyalkyl]acid phosphate compound is particularly preferable, and by combining 4-(meth)acryloyloxyethyltrimellitic acid with bis[2-(meth)acryloyloxyethyl]acid phosphate, heat stability, permeability into tooth substances and bond strength become particularly excellent. Especially by the use of such phosphate-based compounds as previously described, excellent bond property even to an uncut tooth substance is exhibited.

In the case of the combination of 4-(meth)acryloyloxyethyltrimellitic acid and bis[2-(meth)acryloyloxyethyl]acid phosphate, they are used in a weight ratio of usually 10:90 to 90:10, preferably 20:80 to 80:20, particularly preferably 30:70 to 70:30.

The polymerizable monomer (A) is used in an amount of usually 1 to 40% by weight, preferably 3 to 35% by weight, particularly preferably 4 to 30% by weight, in 100% by weight of the self-etching primer composition (V). If the amount of the polymerizable monomer (A) is less than the lower limit of the above range, bond strength is sometimes lowered, and if the amount thereof is more than the upper limit of the above range, stability is sometimes lowered.

As the reducing inorganic compound (B) containing sulfur, which is used to form the self-etching primer composition (V) together with the polymerizable monomer (A), a compound which is used as a redox polymerization initiator when a radical polymerizable monomer is polymerized in a medium such as water is preferably used. Examples of such reducing inorganic compounds (B) containing sulfur include sulfurous acid, bisulfurous acid, metasulfurous acid, metabisulfurous acid, pyrosulfurous acid, thiosulfuric acid, 1-dithionous acid, 1,2-thionic acid, hyposulfurous acid, hydrosulfurous acid and salts of these acids. Of these, sulfites are preferable, and sodium sulfite, potassium sulfite, sodium hydrogensulfite and potassium hydrogensulfite are particularly preferable in the invention. These reducing inorganic compounds (B) can be used singly or in combination. Further, other reducing inorganic compounds or reducing organic compounds can be used in combination within limits not detrimental to the properties of the reducing inorganic compounds (B).

In 100% by weight of the self-etching primer composition (V), the reducing inorganic compound (B) containing sulfur is used in an amount of usually 0.1 to 10% by weight, preferably 0.3 to 8% by weight, particularly preferably 0.5 to 5% by weight. If the amount of the compound (B) is less than the lower limit of the above range, bond property is sometimes lowered, and if the amount thereof is more than the upper limit of the above range, stability is sometimes lowered.

The component (C) to form the self-etching primer composition (V) together with the polymerizable monomer (A) and the reducing inorganic compound (B) containing sulfur is a ketone-based solvent (C).

As the ketone-based solvent (C), a ketone-based compound having no conspicuous harmfulness in the dental field is used. Examples of such ketone-based solvents (C) include acetone, methyl ethyl ketone, diethyl ketone, methyl propyl ketone, ethyl propyl ketone and dipropyl ketone. In the present invention, it is particularly preferable to use acetone which is easily evaporated, has good compatibility with the polymerizable monomer (A) or water (D) and is not found to have conspicuous harmfulness. Such ketone-based solvents (C) can be used singly or in combination.

In 100% by weight of the self-etching primer composition (V), the ketone-based solvent (C) is used in an amount of usually 5 to 50% by weight, preferably 10 to 50% by weight, particularly preferably 15 to 50% by weight. If the amount of the ketone-based solvent (C) is less than the lower limit of the above range, the resulting composition is liable to become ununiform, and if the amount thereof is more than the upper limit of the above range, the resulting composition is liable to have poor solubility.

The component (D) which is used together with the above components in the self-etching primer composition (V) is water. Examples of water (D) employable herein include purified water (Japanese Pharmacopoeia), distilled water, ion-exchanged water and an isotonic sodium chloride solution. Of these, distilled water or ion-exchanged water is preferably used.

In 100% by weight of the self-etching primer composition (V), water (D) is used in an amount of usually 25 to 75% by weight, preferably 25 to 70% by weight, particularly preferably 30 to 70% by weight. If the amount of water (D) is less than the lower limit of the above range, bond property is sometimes lowered, and if the amount thereof is more than the upper limit of the above range, the resulting composition is liable to become ununiform.

The self-etching primer composition (V) used herein does not substantially contain an alcohol. The expression "does not substantially contain" means that an alcohol having been incorporated into the composition together with raw material components, etc. is eliminated to the utmost, not to mention that any alcohol is not added positively. Therefore, even if an alcohol is contained in the self-etching primer composition (V), the amount of the alcohol is not more than 2.5% by weight, and in many cases, the amount is not more than 2% by weight, particularly not more than 1.5% by weight. If an alcohol is contained in a larger amount than this, the self-etching primer composition (V) loses its function. In particular, ethanol is strictly prohibited.

The self-etching primer composition (V) used herein comprises the polymerizable monomer (A), the reducing inorganic compound (B) containing sulfur, the ketone-based solvent (C) and water (D), as described above, and has properties that when a mixture of these components is maintained at a temperature of 65° C., the mixture (composition (V)) can be kept in a stable state for usually not shorter than 2 hours, preferably not shorter than 4 hours, particularly preferably not shorter than 8 hours. The term "storage stability" referred to herein means that the composition does not suffer variation such as gelation or increase of viscosity after the composition is exposed to a temperature of 65° C.

Specifically, a composition having been exposed to a temperature of 65° C. for a given period of time is used. Separately from this, bovine dentin is abraded with water-resistant emery paper #180 under manual pressure with pouring water to form a flat surface. From this flat surface, water is removed by the use of an air syringe. Onto the abraded surface, the self-etching primer composition (V) that is an object of the test is applied, and the composition is allowed to stand still for 20 seconds and dried for 3 seconds. On the thus primer-treated surface, a diameter of a bond area is regulated to 4.8 mm, then a mixture of Super Bond (registered trademark, available from Sun Medical Co., Ltd.) is heaped up thereon, and a polyacrylic cylinder is placed thereon for 5 seconds under manual pressure to compression bond them. After the lapse of one hour, they are immersed in water at 37° C. for 16 hours and then subjected to a tensile bond test (crosshead speed: 2 min/min) A self-etching primer composition exhibiting a tensile strength of not less than 15 MPa to the bovine dentin has storage stability of not shorter than 2 hours at 65° C.

Since the self-etching primer composition (V) has storage stability as above, it can be stably kept over a long period of time at room temperature (e.g., 25° C.). Hence, use of the self-etching primer composition (V) for long-term storage at room temperature is possible.

Although the self-etching primer composition (V) used herein is formed from such components as above and has specific storage stability, other components can be added to this self-etching primer composition (V).

In addition to the above components, a sulfinic acid-based compound can be added as (E) a reducing organic compound component containing sulfur to the self-etching primer composition (V). Examples of the reducing organic compound components (E) containing sulfur, which can be used herein, include aromatic sulfinic acids, such as benzenesulfinic acid, o-toluenesulfinic acid, p-toluenesulfinic acid, ethylbenzenesulfinic acid, decylbenzenesulfinic acid, dodecylbenzenesulfinic acid, chlorobenzenesulfinic acid and naphthalenesulfinic acid, and their salts (Li, Na, K, Mg, Ca, etc.). As the reducing organic compound component (E) containing sulfur used herein, p-toluenesulfinic acid or its salt is preferable, and sodium p-toluenesulfinate is particularly preferable. The reducing organic compound component (E) containing sulfur is used in an amount of usually 0.2 to 20% by weight, preferably 0.5 to 10% by weight, particularly preferably 1 to 5% by weight, based on 100% by weight of the self-etching primer composition (V).

In addition to the above components, the following components can be further contained in the self-etching primer composition (V), within limits not detrimental to the properties of this composition. That is to say, there can be contained:

organic peroxides, such as benzoyl peroxide (BPO), lauryl peroxide, cumene peroxide and t-butyl hydroperoxide, or inorganic peroxides, such as hydrogen peroxide, ammonium persulfate, potassium persulfate, potassium chlorate and perphosphoric acid;

reducing organic compounds, such as aliphatic secondary or tertiary amines, specifically, N,N-dimethylaminoethyl methacrylate, N,N-dimethyl-p-toluidine and N-phenylglycine;

protein crosslinking agents, such as formaldehyde and glutaraldehyde;

storage stabilizers, such as hydroquinone, hydroquinone monomethyl ether, hydroxymethoxybenzoquinone and butylated hydroxytoluene; thickening agents using polymers; and inorganic or organic fillers.

It is also possible to further add a reducing organic compound.

In the present invention, the self-etching composition (V) comprising such components as above is used in the following manner. For example, a fresh tooth substance is abraded with water-resistant emery papers up to #180 by the use of an abrasion device under manual pressure with pouring water to obtain a flat surface of enamel and dentin. Then, water is removed from the surface by the use of an air syringe. To the abraded surface, the self-etching primer composition is applied, and the composition is allowed to stand still for about 20 seconds and dried for about 3 seconds to form a primer layer composed of the self-etching primer composition (V) on the tooth substance surface.

To the primer layer composed of the self-etching primer composition (V), the reaction-curable adhesive composition of the invention is applied, whereby the layer formed from the self-etching primer composition (V) exerts an anchor effect on the tooth substance. Further, since the primer layer composed of the self-etching primer composition (V) has very excellent compatibility with the reaction-curable adhesive composition, the tooth substance and a cured product of the reaction-curable adhesive composition are extremely firmly bonded to each other.

To the dental kit of the invention, the self-etching primer composition (V) described above in detail may be added.

In the present invention, evaluation of bond performance is carried out in the following manner unless otherwise specified.

An example of an adhesion test method is as follows. Bovine dentin is abraded with water-resistant emery papers up to #180 under manual pressure with pouring water to obtain a smooth surface. From this smooth surface, water is removed by the use of an air syringe. To the abraded surface thus formed, the primer composition (III) comprising the polymerizable monomer (a), the aromatic tertiary amine (e) and the water-soluble medium (f) is applied, and the composition is allowed to stand still for 20 seconds and dried for 3 seconds by an air syringe.

On the surface thus primer-treated with the primer composition (III), a bond area is defined to have a diameter of 4.8 mm, then a kneadate of the weakly acidic to alkaline composition (I) and the strongly acidic composition (II) of the invention is heaped up thereon, and a polyacrylic cylinder (abbreviated to "acrylic bar" or "acrylic" hereinafter) is placed thereon for 5 seconds under manual pressure to compression bond them.

After the lapse of one hour, the thus treated bovine dentin is immersed in water at 37° C. for 16 hours and then subjected to a tensile bond test (crosshead speed: 2 mm/min).

An example of a sealing test method is as follows. A bovine tooth was abraded with water-resistant emery papers up to #600 under manual pressure with pouring water so as to expose enamel and dentin, whereby a smooth surface was obtained. Then, a cavity of 3 mm (diameter)×3 mm was formed by the use of a diamond point with pouring water.

The reaction-curable adhesive composition (IV) of the invention consisting of the weakly acidic to alkaline composition (I) and the strongly acidic composition (II) was applied to the surface of the cavity by the use of a sponge, and air was lightly blown.

Thereafter, the composition thus applied was irradiated with light by the use of a visible light irradiation machine (CANDELUX, manufactured by J. MORITA MFG. CORP.), when needed. Subsequently, the cavity was filled with a composite resin Absolute DENTIN (available from Perkel Co.) of dual polymerization type, and the resin was allowed to stand still for 30 minutes at room temperature to cure the resin.

The surface was abraded up to #600 with pouring water to make the surface smooth. Thereafter, the thus treated bovine tooth was immersed in a basic fuchsine aqueous solution for 1 minute and washed with water. Then, the surface was dried by an air syringe, and a gap was observed by a light microscope. Further, coloring perceived at the portion where a gap had been formed was visually observed, and presence or absence of a gap was judged.

As the pH values of the compositions, pH values directly measured are used. If direct measurement is difficult, each composition is diluted with water or an aqueous solvent obtained by adding a hydrophilic solvent such as an alcohol or acetone to water if necessary, then a pH value is actually measured, and from the actually measured value, a change of pH value due to the dilution is discounted to obtain a predicted value. This predicted value may be used as the pH value of the composition. The filler is insoluble, so that calculation is carried out excluding the weight of the filler. As the pH measuring device, a pH meter is preferably used because of precise measurement. As a simple and easy method, use of a pH test paper such as a litmus paper is available. As a more simple and easy method, a method comprising bringing a pH test paper having been wetted with water (the above dilution effect due to water is neglected) into contact with a composition to be measured, comparing the color of the test paper changed with colors of a colorimetry table and judging it with the naked eye.

EXAMPLES

Examples are described below, but it should be construed that the invention is in no way limited to those examples. Abbreviations of the compounds used in the examples described below are as follows.

MMA: methyl methacrylate
HEMA: 2-hydroxyethyl methacrylate
4-META: 4-methacryloyloxyethyltrimellitic anhydride
4-MET.Ca: calcium salt of 4-methacryloyloxyethyltrimellitic acid
2.6E: 2,2-bis(4-methacryloyloxypolyethoxyphenyl)propane
TEGDMA: triethylene glycol dimethacrylate
VR90: Lipoxy 90, available from Showa Highpolymer Co., Ltd.
Bis-GMA: adduct of 1 mol of bisphenol A with 2 mol of glycidyl methacrylate
p-TSNa: sodium p-toluenesulfinate
DMTPO: diphenyl(2,4,6-trimethylbenzoyl)phosphine oxide
UDMA: 1,6-bis(methacryloxyethyloxycarbonylamino)-2,2,4-trimethylhexane
RDMA: 1,3-dimethacryloxyethoxybenzene
NPG.Na: sodium salt of N-phenylglycine
DMPT: N,N-dimethyl-p-toluidine 1 μmBa—$SiO_2$: available from SHOTT Co., Ltd., trade name: SHOTT Barium Glass 8235
7 nm$SiO_2$: available from Nippon Aerosil Co., Ltd, trade name: R812
BPO: benzoyl peroxide
CQ: camphorquinone Measurement of Property Values
Measuring Method of pH of Composition A small amount of a composition is brought into contact with a pH test paper having been wetted with distilled water, and the color changed is confirmed with the naked eye through colorimetry.

Accelerated Storage Test of Composition

A composition is placed in a light-shielding glass container or a resin syringe (manufactured by Terumo Corporation) and stored in a constant-temperature room at 76° C. Appearance of the composition is periodically examined, and a cured state of the composition is confirmed by a contact test using a probe or extrudability from the syringe.

Room Temperature Storage Test of Composition

A composition is placed in a light-shielding glass container or a resin syringe (manufactured by Terumo Corporation) and stored in a constant-temperature room at 23° C. Appearance of the composition is periodically examined, and a cured state of the composition is confirmed by a contact test using a probe or extrudability from the syringe.

Curing Time Measuring Test

Evaluation of curing time was carried out by the following two methods.

First Method

Penetration method comprising allowing a tip of a probe to periodically penetrate the composition with curing the composition of the invention filled in a mold and judging the curing time from the degree of hardness.

Second Method

The curing time was evaluated by DSC method comprising measuring heat of polymerization generated by radical polymerization through differential thermal analysis with curing the composition of the invention filled in a mold.

Preparation of Composition

The composition of the example described in the table was prepared in the following manner. The components were sufficiently mixed in a mortar to prepare a composition in the form of a homogeneous solution or paste. The composition was filled in a syringe having a volume of not more than 10 ml and stored in a refrigerator. For the practical use, the syringe was allowed to stand still for not shorter than 15 minutes at room temperature (about 23° C.) to return the temperature of the solution or the paste to room temperature.

Curing Time

The curing time was measured by the penetration method and the DSC method.

In the penetration method, the curing time indicates a period of time from the beginning of mixing until the composition is so cured as to become non-penetrable by the probe. Completion of curing was measured in the following manner. That is to say, a Teflon (registered trademark) mold having a hole of 4.9 mm (diameter)×1 mm, which had been fixed onto a glass plate, was filled with a curable composition obtained by blending or mixing the components, and the composition was lightly pressure-welded through a polyester film having a thickness of 20 μm. Then, a period of time from the beginning of mixing until the composition is so cured as to become non-penetrable by the probe through the polyester film was measured, and this period of time was regarded as a curing time.

In the DSC method, an exothermic peak caused by radical polymerization performed from the beginning of mixing was measured, and using 10 mg of a sample, a time to reach a maximum peak was measured. A composition having a shorter time to reach the peak and a higher peak intensity has higher curing performance. As the measuring device, a differential scanning calorimeter (manufactured by Shimadzu Corporation, DSC-60) was used.

Bond Strength to Tooth Substance

A fresh bovine mandibular front tooth, which had been extracted, frozen in water and stored, was used as a tooth substance sample. The bovine tooth having been thawed was abraded with water-resistant emery papers up to #180 by the use of a rotary abrasion machine ECOMET-III (manufactured by BUEHLER Co.) under manual pressure with pouring water so that the dentin would be exposed, whereby a smooth surface was obtained. This surface was sufficiently washed with water, then water was removed once by an air syringe, and immediately, a Cellophane tape having a circular hole of 4.9 mm diameter to define a bond area was applied to the surface. If necessary, to the abraded surface having been area-defined was applied a primer composition (III) consisting of a polymerizable monomer (a), an aromatic tertiary amine (e) and an aqueous medium (f), and the composition was allowed to stand still for 20 seconds and dried for 3 seconds by an air syringe.

A Teflon (registered trademark) mold having a hole of 4.9 mm diameter for applying the curable composition of the invention was fixed, and the curable composition was applied. Subsequently, the mold was filled with a composite resin Absolute DENTIN (available from Perkel Co.) of dual polymerization type, and the composite resin was pressure-welded by a glass plate through a polyester film and allowed to stand still for about 30 minutes at room temperature to cure the resin. The polyester film was removed, and onto the cured surface, a polyacrylic cylinder (abbreviated to "acrylic bar" or "acrylic" hereinafter) was fixed with Super Bond (available from Sun Medical Co., Ltd.). After the lapse of one hour, they were immersed in water at 37° C. for 16 hours and then subjected to a tensile bond test (crosshead speed: 2 mm/min).

Sealing Test

A fresh bovine mandibular front tooth, which had been extracted, frozen in water and stored, was used as a tooth substance sample. A tooth crown part of the bovine tooth having been thawed was cut by a rotary diamond cutter ISOMET (manufactured by BUEHLER Co.) with pouring water, and a tooth root from which a dental pulp had been removed was used. The tooth root was drilled from the tooth crown side with pouring water to form a dental pulp cavity having a diameter of 4 mm and a depth of about 20 mm. If necessary, the cavity was filled with the composition (III) of the invention by the use of a syringe having a syringe needle, then the composition was brought into contact with a root canal wall sufficiently by the use of a microbrush, and after about 30 seconds, the composition was suction-removed. Then, the cavity was filled with the reaction-curable adhesive composition (III) (mixture of weakly acidic to alkaline composition (I) and strongly acidic composition (II)) of the invention by a syringe having a syringe needle in the same manner as above, and the curable composition present inside the root canal was removed by a paper point. At this time, it was confirmed that the curable composition was present on the dentin surface inside the root canal to such an extent that glossiness remained. Thereafter, if necessary, light irradiation was carried out from the tooth crown side by the use of a visible light irradiation machine (CANDELUX, manufactured by J. MORITA MFG. CORP.). Subsequently, the cavity was closely filled with a composite resin (trade name: Metafil C, available from Sun Medical Co., Ltd.) having a diameter of 3 mm and a height of 20 mm, which had been previously cured, and a composite resin Absolute DENTIN (available from Perkel Co.) of dual polymerization type, and they were allowed to stand still for 30 minutes at room temperature to cure the resin. The tooth root was cut in round slices at the position of 5 mm below from the tooth crown part side, and the cut surface was abraded up to #600 with pouring water to make the surface smooth. Thereafter, the slice was immersed in a basic fuchsine aqueous solution for 24 hours and washed with water.

The thus treated slice was dried by an air syringe, and a gap formed between the tooth root part and the curable composition was observed by a light microscope.

Since the portion where a gap had been formed was found to have been colored, a ratio of the uncolored (unsealed) portion to the length of the circumference of the bonded portion was calculated as a sealing ratio (%). A sealing ratio of 100% is desirable, and a sealing ratio of less than 50% is undesirable.

Example 1

A strongly acidic composition (II) having a pH value of 1.5 shown in Table 1 and a weakly acidic to alkaline composition (I) having a pH value of 6.55 shown in Table 1 were prepared, and they were each independently introduced into a resin syringe (manufactured by Terumo Corporation) of 10 ml and subjected to an accelerated storage test and a room temperature storage test. As a result, in the accelerated storage test, marked discoloration was not observed even after the lapse of one week, extrudability was excellent, and neither gelation nor curing was observed. In the room temperature storage test in a light-shielded state, neither gelation nor curing was observed even after storage of 3 months.

0.15 Part by weight of the strongly acidic composition (II) having a pH value of 1.5 shown in Table 1 and 0.15 part by weight of the weakly acidic to alkaline composition (I) having a pH value of 6.5 shown in Table 1 were taken out into a Dappen dish and mixed therein. When they were stirred by a spatula, they could be easily mixed in a necessary mixing time of about 10 seconds, and the resulting mixture exhibited a pH value of 3. The curing time as measured by the penetration method was about 30 minutes, the bond strength was 4.5 MPa, and the sealing ratio was 65%. The results are set forth in Table 1.

Comparative Example 1

In the process of Example 1, bond strength was measured by directly filling the composite resin Absolute DENTIN (available from Perkel Co.) of dual polymerization type without using the curable composition. As a result, peeling took place during immersion in water, so that the bond strength was regarded as 0 (zero). The sealing ratio was about 20%. The results are set forth in Table 1.

Comparative Example 2

The same tests as in Example 1 were carried out, except that the pH value of the weakly acidic to alkaline composition (I) was adjusted to 4 by the use of hydrochloric acid. The curing time as measured by the penetration method was about 20 minutes, the bond strength was 6 MPa, and the sealing ratio was 70%. In the accelerated storage test, however, gelation took place in about 30 minutes, and in the room temperature storage test, gelation took place in about 24 hours, and the mixture could not be extruded.

Examples 2 to 5

A weakly acidic to alkaline composition (I) having a pH value shown in Table 1 and a strongly acidic composition (II) having a pH value shown in Table 1 were prepared, and they were each independently introduced into a resin syringe (manufactured by Terumo Corporation) of 10 ml and subjected to an accelerated storage test and a room temperature storage test.

As a result, in the accelerated storage test, marked discoloration was not observed even after the lapse of one week, extrudability was excellent, and neither gelation nor curing was observed. In the room temperature storage test in a light-shielded state, neither gelation nor curing was observed even after storage of 3 months.

0.15 Part by weight of the weakly acidic to alkaline composition (I) shown in Table 1 and 0.15 part by weight of the strongly acidic composition (II) shown in Table 1 were taken out into a Dappen dish and mixed therein. When they were stirred by a spatula, they could be easily mixed in a necessary mixing time of about 10 seconds. The pH value, curing time as measured by the penetration method, bond strength and sealing ratio of the resulting mixture are as shown in Table 1.

of about 30 seconds. The pH value, curing time as measured by the DSC method, bond strength and sealing ratio of the resulting mixture are as shown in Table 2.

TABLE 2

|  |  |  | Ex. 6 | Ex. 7 |
| --- | --- | --- | --- | --- |
| Composition (I) | Polymerizable monomer (a) | TEGDMA | 40 | 40 |
|  | Filler (b) | 1 µm Ba•SiO$_2$ | 45 | 45 |
|  |  | 7 nm SiO$_2$ | 6 | 6 |
|  | Salt of organic acid (b) | NPG•Na | 3 | 9 |
|  |  | P-TSNa | 6 | — |
|  | pH of composition (I) | pH value | 6.5 | 6.5 |
| Composition (II) | Polymerizable monomer (a) | 4-META | 6 | 6 |
|  |  | HEMA | 11.8 | 11.8 |
|  |  | 2.6E | 4.5 | 4.5 |
|  |  | TEGDMA | 3 | 3 |
|  |  | VR90 | 4.5 | 4.5 |
|  | Filler (b) | TMPT-f | 3.5 | 3.5 |
|  |  | 3 µm SiO$_2$ | 38.5 | 38.5 |
|  |  | 1 µm Ba•SiO$_2$ | 28 | 28 |
|  | Reaction initiator (c) | BPO | 0.2 | 0.2 |
|  |  | CQ | — | — |
|  | pH of composition (II) | pH value | 6.5 | 6.5 |
|  | Mixing ratio (I):(II) |  | 80:20 | 80:20 |

TABLE 1

|  |  |  | Ex. 1 | Ex. 2 | Ex. 3 | Ex. 4 | Ex. 5 | Comp. Ex. 1 | Comp. Ex. 2 |
| --- | --- | --- | --- | --- | --- | --- | --- | --- | --- |
| Composition (I) | Polymerizable monomer (a) | HEMA | 95 | 95 | 95 | 97 | — | — | 95 |
|  |  | TEGDMA | — | — | — | — | 96.5 | — | — |
|  | Salt of organic acid (b) | NPG•Na | 5 | 5 | 5 | 3 | 3 | — | 5 |
|  |  | DMPT | — | — | — | — | 0.5 | — | *1 |
|  | pH of composition (I) | pH value | 6.5 | 6.5 | 6.5 | 4.5 | 4.5 | — | 4 |
| Composition (II) | Polymerizable monomer (a) | 4-META | 40 | 40 | 40 | 40 | 40 | — | 40 |
|  |  | HEMA | 60 | 59 | 59 | 59 | 59 | — | 59 |
|  | Reaction initiator (c) | BPO | — | 1 | — | 1 | 1 | — | — |
|  |  | CQ | — | — | 1 | — | — | — | — |
|  | pH of composition (II) | pH value | 1.5 | 1.5 | 1.5 | 1.5 | 1.5 | — | 1.5 |
| Mixing ratio (I):(II) |  |  | 50:50 | 50:50 | 50:50 | 50:50 | 50:50 | — | 50:50 |
| pH value of mixture |  |  | 3 | 3 | 3 | 3 | 3 | — | 1 |
| (I) + (II) curing time (min) |  |  | 30 | 18 | 30 | 17 | 13 | — | 20 |
| Bond strength (MPa) |  |  | 4.5 | 5 | 6 | 4.5 | 5 | 0 | 6 |
| Sealing ratio (%) |  |  | 65 | 70 | 80 | 65 | 70 | 20 | 70 |

Notes:
In Comparative Example 2, to 5 parts by weight of the salt of organic acid was further added 6N-HCL to adjust the pH value of the composition (I) to 4.

Examples 6 and 7

A weakly acidic to alkaline composition (I) having a pH value shown in Table 2 and a composition (II) having a pH value shown in Table 2 were prepared, and they were each independently introduced into a resin syringe (manufactured by Terumo Corporation) of 10 ml and subjected to an accelerated storage test and a room temperature storage test. As a result, in the accelerated storage test, marked discoloration was not observed even after the lapse of one week, extrudability was excellent, and neither gelation nor curing was observed. In the room temperature storage test in a light-shielded state, neither gelation nor curing was observed even after storage of 3 months.

0.8 Part by weight of the weakly acidic to alkaline composition (I) shown in Table 2 and 0.2 part by weight of the strongly acidic composition (II) shown in Table 2 were taken out on a mixing paper and mixed thereon by a spatula. As a result, they could be easily mixed in a necessary mixing time TABLE 2-continued

|  | Ex. 6 | Ex. 7 |
| --- | --- | --- |
| pH value of mixture | 3.5 | 3.5 |
| (I) + (II) curing time (min) | 3 | 2 |
| Bond strength (MPa) | 5 | 6 |
| Sealing ratio (%) | 80 | 90 |

Examples 8 to 12

A weakly acidic to alkaline composition (I) having a pH value shown in Table 3 and a strongly acidic composition (II) having a pH value shown in Table 3 were prepared, and they were each independently introduced into a resin syringe (manufactured by Terumo Corporation) of 10 ml and subjected to an accelerated storage test and a room temperature storage test. As a result, in the accelerated storage test, marked discoloration was not observed even after the lapse of one week, extrudability was excellent, and neither gelation nor curing was observed. In the room temperature storage test in a light-shielded state, neither gelation nor curing was observed even after storage of 3 months.

Prior to application of the weakly acidic to alkaline composition (I) and the strongly acidic composition (II) to a tooth substance, a primer composition (III) shown in Table 3 was applied to the tooth substance surface. As a result, improvement in bond strength and sealing ratio was observed. The results are as shown in Table 3.

contained as a calcium salt in the weakly acidic to alkaline composition (I).

Prior to application of a mixture of the weakly acidic to alkaline composition (I) and the strongly acidic composition (II) to a tooth substance, a primer composition MD shown in Table 3 was applied to the tooth substance surface. As a result, improvement in bond strength and sealing ratio was observed. The results are as shown in Table 4.

TABLE 3

|  |  |  | Ex. 8 | Ex. 9 | Ex. 10 | Ex. 11 | Ex. 12 |
| --- | --- | --- | --- | --- | --- | --- | --- |
| Composition (I) | Polymerizable monomer (a) | HEMA | 95 | 95 | — | — | — |
|  |  | TEGCDMA | — | — | 96.5 | 40 | 40 |
|  | Filler (b) | 1 µm Ba•SiO$_2$ | — | — | — | 45 | 45 |
|  |  | 7 nm SiO$_2$ | — | — | — | 6 | 6 |
|  | Salt of organic acid (b) | NPG•Na | 5 | 5 | 3 | 3 | 9 |
|  |  | p-TSNa | — | — | 0.5 | 6 | — |
|  | pH of composition (I) | pH value | 6.5 | 6.5 | 6.5 | 6.5 | 6.5 |
| Composition (II) | Polymerizable monomer (a) | 4-MET | 40 | 40 | 40 | — | — |
|  |  | 4-META | — | — | — | 6 | 6 |
|  |  | HEMA | 60 | 59 | 59.6 | 11.8 | 11.8 |
|  |  | 2.6E | — | — | — | 4.5 | 4.5 |
|  |  | TEGDMA | — | — | — | 3 | 3 |
|  |  | VR90 | — | — | — | 4.5 | 4.5 |
|  | Filler (b) | TMPT-f | — | — | — | 3.5 | 3.5 |
|  |  | 3 µm SiO$_2$ | — | — | — | 38.5 | 38.5 |
|  |  | 1 µm Ba•SiO$_2$ | — | — | — | 28 | 28 |
|  | Reaction initiator (c) | BPO | — | 1 | — | 0.2 | 0.2 |
|  |  | CQ | — | — | 0.5 | — | — |
|  | Mixing ratio (I):(II) |  | 50:50 | 50:50 | 50:50 | 80:20 | 80:20 |
|  | pH value of composition (II) |  | 3 | 3 | 3 | 3.5 | 3.5 |
| Composition (III) | Polymerizable monomer (a) | 4-META | 10 | 36 | 35 | — | — |
|  |  | 4-MET | — | — | — | 35 | 35 |
|  |  | UDMA | — | 3.5 | — | — | 3.5 |
|  |  | HEMA | 15 | — | 1 | 1 | 1 |
|  |  | 2.6E | — | — | 3.5 | — | — |
|  |  | Bis-GMA | — | — | — | 3.5 | — |
|  | Aromatic tertiary amine (e) | DEPT | 0.5 | 0.5 | 0.6 | 0.5 | 0.5 |
|  | Aqueous solvent (f) | water | 29.5 | 29.5 | 30 | 30 | 30 |
|  |  | acetone | 45 | 45 | 30 | 30 | 30 |
| (I) + (II) curing time (min) |  |  | 30 | 30 | 30 | 3 | 2 |
| Bond strength (MPa) |  |  | 6 | 6 | 8 | 8 | 7 |
| Sealing ratio (%) |  |  | 80 | 90 | 90 | 95 | 95 |

Examples 13 and 14

A weakly acidic to alkaline composition (I) having a pH value shown in Table 4 and a strongly acidic composition (II) having a pH value shown in Table 4 were prepared, and they were each independently introduced into a resin syringe (manufactured by Terumo Corporation) of 10 ml and subjected to an accelerated storage test and a room temperature storage test. As a result, in the accelerated storage test, marked discoloration was not observed even after the lapse of one week, extrudability was excellent, and neither gelation nor curing was observed. In the room temperature storage test in a light-shielded state, neither gelation nor curing was observed even after storage of 3 months.

In these examples, storage became possible by adjusting a pH value of the composition even in the use of the polymerizable monomer (a1) having an acidic group, as can be understood from the fact that the neutralized component (a2) was

TABLE 4

|  |  |  | Ex. 13 | Ex. 14 |
| --- | --- | --- | --- | --- |
| Composition (I) | Polymerizable monomer (a) | TEGCDMA | 40 | 40 |
|  |  | 4-MET•Ca | 3 | 3 |
|  | Filler (b) | 1 µm Ba•SiO$_2$ | 45 | 45 |
|  |  | 7 nm SiO$_2$ | 3 | 3 |
|  | Salt of organic acid (b) | NPG•Na | 3 | 3 |
|  |  | p-TSNa | 6 | 6 |
|  | pH of composition (I) | pH value | 6.5 | 6.5 |
| Composition (II) | Polymerizable monomer (a) | 4-META | 6 | 6 |
|  |  | HEMA | 11.8 | 11.8 |
|  |  | 2.6E | 4.5 | 4.5 |
|  |  | TEGDMA | 3 | 3 |
|  |  | VR90 | 4.5 | 4 |
|  | Filler (b) | TMPT-f | 3.5 | 3.5 |
|  |  | 3 µm SiO$_2$ | 38.5 | 38.5 |
|  |  | 1 µm Ba•SiO$_2$ | 28 | 28 |
|  | Reaction initiator (c) | BPO | 0.2 | 0.2 |
|  |  | CQ | — | 0.5 |
|  | Mixing ratio (I):(II) |  | 80:20 | 80:20 |
|  | pH value of mixture |  | 3.5 | 3.5 |

TABLE 4-continued

|  |  |  | Ex. 13 | Ex. 14 |
|---|---|---|---|---|
| Composition (III) | Polymerizable monomer (a) | 4-META | 35 | 35 |
|  |  | HEMA | 1 | 1 |
|  |  | UDMA | 3.5 | 3.5 |
|  | Aromatic tertiary amine (e) | DEPT | 0.5 | 0.5 |
|  | Aqueous solvent (f) | Water | 30 | 30 |
|  |  | acetone | 30 | 30 |
| (I) + (II) curing time (min) |  |  | 3 | 3 |
| Bond strength (MPa) |  |  | 13 | 13 |
| Sealing ratio (%) |  |  | 100 | 100 |

Example 15

A weakly acidic to alkaline composition (I) having a pH value shown in Table 5 and a strongly acidic composition (II) having a pH value shown in Table 5 were prepared, and they were each independently introduced into a resin syringe (manufactured by Terumo Corporation) of 10 ml and subjected to an accelerated storage test and a room temperature storage test. As a result, in the accelerated storage test, marked discoloration was not observed even after the lapse of one week, extrudability was excellent, and neither gelation nor curing was observed. In the room temperature storage test in a light-shielded state, neither gelation nor curing was observed even after storage of 3 months.

In these examples, storage became possible by using sodium hydroxide as a pH adjustor in the weakly acidic to alkaline composition (I) and thereby adjusting a pH value of the composition.

Prior to application of a mixture of the weakly acidic to alkaline composition (I) and the strongly acidic composition (II) to a tooth substance, the tooth substance surface was treated with a primer composition (III) shown in Table 3. As a result, improvement in bond strength and sealing ratio was observed. The results are as shown in Table 5.

Comparative Example 3

In Example 15, a weakly acidic to alkaline composition (I) having a pH value shown in Table 5 and a strongly acidic composition (II) having a pH value shown in Table 5 were prepared, and they were each independently introduced into a resin syringe (manufactured by Terumo Corporation) of 10 ml and subjected to an accelerated storage test and a room temperature storage test. The weakly acidic to alkaline composition (I) had a pH value of 4, and differently from Example 15, adjustment of the pH value was not carried out.

As a result, in the accelerated storage test, the weakly acidic to alkaline composition (I) began to gel after 30 minutes from the preparation, and after 1 day, it was cured. The curing time, bond strength and sealing ratio are set forth in Table 5.

TABLE 5

|  |  |  | Ex. 15 | Comp. Ex. 3 |
|---|---|---|---|---|
| Composition (I) | Polymerizable monomer (a) | HEMA | 95 | 95 |
|  | Salt of organic acid (b) | NPG | 5 | 5 |
|  | Adjustment of pH value | pH adjuster | NaOH | — |

TABLE 5-continued

|  |  |  | Ex. 15 | Comp. Ex. 3 |
|---|---|---|---|---|
|  | pH of composition (I) | pH value | 6.5 | 4 |
| Composition (II) | Polymerizable monomer (a) | 4-MET | 40 | 40 |
|  |  | HEMA | 59 | 59 |
|  | pH of composition (II) | pH value | 1.5 | 1.5 |
| Mixing ratio (I):(II) |  |  | 50:50 | 50:50 |
| pH value of mixture |  |  | 1 | 1 |
| (I) + (II) curing time (min) |  |  | 30 | 20 |
| Bond strength (MPa) |  |  | 6 | 7 |
| Sealing ratio (%) |  |  | 85 | 75 |

Example 16

A weakly acidic to alkaline composition (I) having a pH value shown in Example 15 and a strongly acidic composition (II) having a pH value shown in Example 15 were prepared.

Prior to application of a mixture of the weakly acidic to alkaline composition (I) and the strongly acidic composition (II) to a tooth substance, the tooth substance surface was treated with a self-etching primer composition (V) in the form of a solution consisting of 10 parts by weight of 4-MET, 10 parts by weight of bis(2-methacryloyloxyethyl) acid phosphate, 2.5 parts by weight of sodium sulfite, 47.5 parts by weight of purified water and 30 parts by weight of acetone. As a result, the bond strength was 8 MPa and the sealing ratio was 95%, so that both of these properties were improved.

The composition of the invention is very useful in the field of dentistry using bonding material, coating material, opaque material, fissure sealant, cement, lining material, composite resin as sealant, root canal filling (sealing) material, root canal filling sealer, hyperesthesia inhibitor, orthodontic adhesive, abutment construction resin, denture base resin, repairing material for denture base resin, temporary cementation material, temporary sealant, etc. for dental use.

The invention claimed is:

1. A method of using a reaction-curable adhesive composition exhibiting acidity, comprising a step of applying said reaction curable adhesive composition to a tooth surface that has been previously treated with a self-etching primer composition (V) which contains (A) a polymerizable monomer, (B) a reducing inorganic compound containing sulfur, (C) a ketone solvent and (D) water, and which does not substantially contain an alcohol solvent and has storage stability of not shorter than 2 hours at 65° C., wherein said reaction curable adhesive composition comprises:

a weakly acidic to alkaline composition (I), wherein the pH value of said weakly acidic to alkaline composition (I) at 23° C. is in the range of 4.5 to 9, comprising:
(a) a polymerizable monomer and (b) a compound represented by the following formula (1):

$$R^1-C_6H_4-NR^2CH_2COOR^3 \qquad (1)$$

wherein $R^1$ and $R^2$ are each independently a hydrogen atom or an alkyl group which may have a functional group, and $R^3$ is a hydrogen atom or a metal atom, and a strongly acidic composition (II), wherein the pH value of the strongly acidic composition (II) at 23° C. is not less than 0.1 but less than 4.5, comprising:
(a1) a polymerizable monomer having at least one acidic group in a molecule selected from the group consisting of a carboxylic acid group, a phosphoric acid group, a thiophosphoric acid group, a sulfonic acid group, and a sulfinic acid group.

2. The method of using a reaction-curable adhesive composition exhibiting acidity as claimed in claim 1, wherein the polymerizable monomer (A) to constitute the self-etching primer composition (V) is at least one polymerizable monomer selected from the group consisting of 4-(meth)acryloyloxyalkyltrimellitic acid, bis{(meth)acryloyloxyalkyl}acid phosphate, and acid anhydrides thereof,
the reducing inorganic compound (B) containing sulfur is sulfurous acid and/or a salt thereof, and
the self-etching primer composition (V) contains the polymerizable monomer (A) in an amount of 1 to 40% by weight, the reducing inorganic compound (B) containing sulfur, in an amount of 0.1 to 10% by weight, the ketone solvent (C) in an amount of 5 to 50% by weight and water (D) in an amount of 25 to 75% by weight.

3. The method of using a reaction-curable adhesive composition exhibiting acidity as claimed in claim 2, wherein the self-etching primer composition (V) further contains a sulfinic acid compound as (E) a reducing organic compound component containing sulfur.

4. The method of using a reaction-curable adhesive composition exhibiting acidity as claimed in claim 1, wherein the polymerizable monomer (a) contains (a1) a polymerizable monomer having an acidic group in a molecule.

5. The method of using a reaction-curable adhesive composition exhibiting acidity as claimed in claim 1, wherein the polymerizable monomer (a) contains (a2) a polymerizable monomer in which an acidic group in a molecule has been neutralized with a calcium ion.

6. The method of using a reaction-curable adhesive composition exhibiting acidity as claimed in claim 1, wherein the pH value of the reaction-curable adhesive composition exhibiting acidity, which comprises the weakly acidic to alkaline composition (I) and the strongly acidic composition (II), at 23° C. is in the range of 0.5 to 6.

7. The method of using a reaction-curable adhesive composition exhibiting acidity as claimed in claim 1, wherein the compound (b) represented by the formula (1) is (b1) a salt of N-phenylglycine.

8. The method of using a reaction-curable adhesive composition exhibiting acidity as claimed in claim 1, wherein the weakly acidic to alkaline composition (I) and/or the strongly acidic composition (II) contains (c) a polymerization initiator.

9. The method of using a reaction-curable adhesive composition exhibiting acidity as claimed in claim 8, wherein the polymerization initiator (c) contained in the weakly acidic to alkaline composition (I) contains a reducing compound (c1) other than the compound (b) represented by the formula (1).

10. The method of using a reaction-curable adhesive composition exhibiting acidity as claimed in claim 9, wherein the reducing compound (c1) contained in the weakly acidic to alkaline composition (I) contains (c11) an organic sulfinic acid compound, and/or (c12) a barbituric acid compound.

11. The method of using a reaction-curable adhesive composition exhibiting acidity as claimed in claim 10, wherein the reducing compound (c1) contained in the weakly acidic to alkaline composition (I) contains the organic sulfinic acid compound (c11), and the blending weight ratio (b)/(c11) of the compound (b) represented by the formula (1) to the organic sulfinic acid compound contained in the weakly acidic to alkaline composition (I) is in the range of 0.05 to 20.

12. The method of using a reaction-curable adhesive composition exhibiting acidity as claimed in claim 1, wherein the polymerization initiator (c) contained in the strongly acidic composition (II) is (c2) a photopolymerization initiator and/or (c3) a peroxide polymerization initiator.

13. The method of using a reaction-curable adhesive composition exhibiting acidity as claimed in claim 1, wherein the weakly acidic to alkaline composition (I) and/or the strongly acidic composition (II) contains (d) a filler.

14. A dental adhesive kit comprising:
a weakly acidic to alkaline composition (I) comprising (a) a polymerizable monomer and (b) a compound represented by the following formula (1):

$$R^1-C_6H_4-NR^2CH_2COOR^3 \qquad (1)$$

wherein $R^1$ and $R^2$ are each independently a hydrogen atom or an alkyl group which may have a functional group, and $R^3$ is a hydrogen atom or a metal atom,
a strongly acidic composition (II) comprising (a1) a polymerizable monomer having at least one acidic group in a molecule selected from the group consisting of a carboxylic acid group, a phosphoric acid group, a thiophosphoric acid group, a sulfonic acid group, and a sulfinic acid group, and
a primer composition (III),
wherein the pH value of the weakly acidic to alkaline composition (I) at 23° C. is in the range of 4.5 to 9,
wherein the pH value of the strongly acidic composition (II) at 23° C. is not less than 0.1 but less than 4.5,
wherein the primer composition (III) comprises (a) a polymerizable monomer, (e) an aromatic tertiary amine and (f) a water-soluble solvent, and
wherein the weakly acidic to alkaline composition (I), the strongly acidic composition (II) and the primer composition (III) are separately packaged.

15. The dental adhesive kit as claimed in claim 14, wherein the polymerizable monomer (a2) in which an acidic group in a molecule has been neutralized with a calcium ion is contained in any one of the weakly acidic to alkaline composition (I), the strongly acidic composition (II) and the primer composition (III).

16. The dental adhesive kit as claimed in claim 14, wherein the compound (b) represented by the formula (I), which is contained in the weakly acidic to alkaline composition (I), is (b1) a salt of N-phenylglycine.

17. The dental adhesive kit as claimed in claim 14, wherein a reducing compound (c1) is contained in the weakly acidic to alkaline composition (I), and the reducing compound (c1) contains
(c11) an organic sulfinic acid compound, and/or
(c12) a barbituric acid compound.

18. The dental adhesive kit as claimed in claim 14, wherein the reducing compound (c1) contained in the weakly acidic to alkaline composition (I) contains the organic sulfinic acid compound (c11), and the blending weight ratio [(b)/(c11)] of the compound (b) represented by the formula (I) to the organic sulfinic acid compound contained in the weakly acidic to alkaline composition (I) is in the range of 0.05 to 20.

19. The dental adhesive kit as claimed in claim 14, further comprising a self-etching primer composition (V) which is used for previously treating a reaction-curable adhesive composition application surface, contains (A) a polymerizable monomer, (B) a reducing inorganic compound containing sulfur, (C) a ketone solvent and (D) water, does not substantially contain an alcohol solvent and has storage stability of not shorter than 2 hours at 65° C.

20. The dental adhesive kit as claimed in claim 19, wherein the polymerizable monomer (A) to constitute the self-etching primer composition (V) is at least one polymerizable monomer selected from the group consisting of 4-(meth)acryloyloxyalkyltrimellitic acid, his {(meth)acryloyloxyalkyl}acid phosphate, and acid anhydrides thereof, the reducing inorganic compound (B) containing sulfur is sulfurous acid and/or a salt thereof, and the self-etching primer composition (V) contains the polymerizable monomer (A) in an amount of 1 to 40% by weight, the reducing inorganic compound (B) containing sulfur, in an amount of 0.1 to 10% by weight, the ketone solvent (C) in an amount of 5 to 50% by weight and water (D) in an amount of 25 to 75% by weight.

21. The dental adhesive kit as claimed in claim 20, wherein the self-etching primer composition (V) further contains a sulfinic acid compound as (E) a reducing organic compound component containing sulfur.

\* \* \* \* \*

UNITED STATES PATENT AND TRADEMARK OFFICE
CERTIFICATE OF CORRECTION

PATENT NO.        : 8,297,975 B2                                  Page 1 of 1
APPLICATION NO.   : 12/599821
DATED             : October 30, 2012
INVENTOR(S)       : Takashi Yamamoto et al.

It is certified that error appears in the above-identified patent and that said Letters Patent is hereby corrected as shown below:

Face of the Patent, Column 2, Item (57) Abstract, Line 4, delete "(I)" and insert -- (1) --

Column 34, Line 53, Claim 18, delete "(I)" and insert -- (1) --

Column 35, Line 1, Claim 20, delete "his {(meth)" and insert -- bis{(meth) --

Signed and Sealed this
Twenty-second Day of January, 2013

David J. Kappos
*Director of the United States Patent and Trademark Office*